United States Patent
Rosario-Melendez et al.

(10) Patent No.: US 10,687,601 B2
(45) Date of Patent: *Jun. 23, 2020

(54) COSMETIC CARE SYSTEM

(71) Applicant: L'ORÉAL, Paris (FR)

(72) Inventors: Roselin Rosario-Melendez, Piscataway, NJ (US); Gisela Perruna, Rahway, NJ (US); Susan Ashley Desteno, Old Bridge, NJ (US); Marcel Sanchez, Aulnay sous Bois (FR)

(73) Assignee: L'OREAL, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 15/223,951

(22) Filed: Jul. 29, 2016

(65) Prior Publication Data

US 2018/0027943 A1 Feb. 1, 2018

(51) Int. Cl.
| | | |
|---|---|---|
| *A45D 34/04* | (2006.01) | |
| *A45D 40/26* | (2006.01) | |
| *A61K 8/891* | (2006.01) | |
| *A61K 8/898* | (2006.01) | |
| *A61K 8/92* | (2006.01) | |
| *A61Q 1/04* | (2006.01) | |

(52) U.S. Cl.
CPC ......... *A45D 34/046* (2013.01); *A45D 34/042* (2013.01); *A45D 40/265* (2013.01); *A45D 40/267* (2013.01); *A61K 8/891* (2013.01); *A61K 8/898* (2013.01); *A61K 8/92* (2013.01); *A61Q 1/04* (2013.01); *A61K 2800/30* (2013.01); *A61K 2800/31* (2013.01); *A61K 2800/43* (2013.01); *A61K 2800/594* (2013.01); *A61K 2800/87* (2013.01)

(58) Field of Classification Search
None
See application file for complete search history.

(56) References Cited

U.S. PATENT DOCUMENTS

| | | |
|---|---|---|
| 5,505,937 A | 4/1996 | Castrogiovanni et al. |
| 5,911,974 A | 6/1999 | Brieva et al. |
| 6,019,962 A | 2/2000 | Rabe et al. |
| 6,027,738 A | 2/2000 | Stepniewski et al. |
| 6,074,654 A | 6/2000 | Drechsler et al. |
| 6,340,466 B1 | 1/2002 | Drechsler et al. |
| 6,387,405 B1 | 5/2002 | Shah et al. |
| 6,555,097 B1 | 4/2003 | Rabe et al. |
| 8,945,525 B2 | 2/2015 | Bradshaw et al. |
| 2003/0049212 A1* | 3/2003 | Robinson ............ A61K 8/06 424/59 |

(Continued)

FOREIGN PATENT DOCUMENTS

WO  WO 2016/046355  3/2016

OTHER PUBLICATIONS

What's That Stuff?, Lipstick, Jul. 12, 1999, vol. 77, No. 28 (Year: 1999).*

(Continued)

*Primary Examiner* — Isis A Ghali
(74) *Attorney, Agent, or Firm* — Polsinelli PC

(57) ABSTRACT

The present invention relates to a cosmetic care system comprising (1) a composition comprising at least one silicone elastomer, at least one non-volatile oil, at least one silicone resin, at least one volatile solvent, at least one polyorganosiloxane copolymer; and (2) and an applicator.

14 Claims, 19 Drawing Sheets

(56) References Cited

U.S. PATENT DOCUMENTS

2007/0053859 A1    3/2007  Bui et al.
2010/0297050 A1   11/2010  Bui et al.
2012/0171138 A1    7/2012  Bradshaw et al.
2012/0272981 A1*  11/2012  Ricard ................ A45D 34/041
                                                             132/200

OTHER PUBLICATIONS

International Search Report and Written Opinion dated Sep. 29, 2017 in corresponding PCT/US2017/043749 filed on Jul. 25, 2017.

* cited by examiner

COSMETIC CARE SYSTEM

FIELD OF THE INVENTION

The present invention relates to a cosmetic care system comprising (1) a composition comprising at least one silicone elastomer, at least one non-volatile oil, at least one silicone resin, at least one volatile solvent, at least one polyorganosiloxane copolymer; and (2) and an applicator. Additionally, the invention relates to a method for making up and/or enhancing the appearance of a keratinous substrate.

BACKGROUND OF THE INVENTION

Cosmetic compositions used to make up or enhance the appearance of a user's skin are often required to be able to impart various properties such as long wear, transfer resistance and comfort. However, the formulation of cosmetic products that can deliver these properties at the same time can pose some challenges. For example, cosmetic compositions using traditional ingredients known to impart long wear, such as silicone resins, are very drying. In addition, they cause discomfort and flaking during the use. In order to overcome these problems, oils, such as silicone oils are generally employed. While the utilization of silicone oils in cosmetics is popular, one drawback associated with their use is that they tend to shine and are tacky, which are not always desired effects for the finished products.

Additional challenges linked to the wear and comfort of the cosmetic products relate to the structure of the applicators used to apply the finished products on the keratinous substrates. For instance, the applicators which are entirely covered with bristles and/or flocks, typically deliver very heavy and uneven deposit of the cosmetics. Such application is not only unattractive but also relates to the undesired discomfort of wear of the finished products.

Therefore, it is an object of the present invention to provide a system of a composition and an applicator which will allow for an evenly spread and nicely contoured application of cosmetic products. It is understood that precise and uniform application will not only be visually aesthetic but also it would decrease the tackiness of the cosmetic and contribute to its superior comfort and longer wear.

It has been surprisingly discovered that the combination of silicone crosspolymer (elastomer) and silicone oil (fluid) at specific ratios in addition to silicone resins, polyorganosiloxane copolymer and volatile solvent, provides the composition(s) characterized by non-tacky feel, transfer resistance, long wear, minimal or absence of flaking and superior comfort when applied onto the keratinous substrates. The compositions of the present inventions are also matte.

Additionally, it has been observed that the use of the inventive applicator having two opposite faces and a partial flocking, delivers a precise and very appealing application of the inventive compositions. The unique system of the inventive composition and the applicator allows for a thin distribution of the inventive products that contributes to its long and comfortable, non-tacky wear.

SUMMARY OF THE INVENTION

The present invention relates to a cosmetic care system comprising;
(1) at least one composition comprising:
(a) from about 1% to about 30% by weight of at least one silicone elastomer;
(b) from about 2% to about 30% by weight of at least one non-volatile oil;
(c) from about 2% to about 35% by weight of polyorganosiloxane copolymer;
(d) from about 5% to about 30% by weight of at least one silicone resin;
(e) from about 5% or about 50% of at least one volatile;
(f) optionally at least one wax;
(g) optionally at least one colorant; and
(h) optionally at least one filler; and
(2) an applicator.

Preferably the inventive composition is an anhydrous composition which is long wearing and transfer resistant, while at the same time provides superior comfort, non-tacky feel and looks matte.

As per another embodiment of the inventive composition, the ratio of the silicone elastomer (a) to the at least one non-volatile oil (b) is higher or equal to from about 1:0.02 and is lower or equals to from about 1:10 by weight (for example, 1:0.02 to 1:10), including all ranges and subranges therebetween such as, for example, from about 1:1 to about 1:6 and from about 1:1 to about 1:5, the weights being relative to the total weight of the composition. All numerical values are weight percent solids (actives).

According to a preferred embodiment, the composition further contains at least one colorant, at least one wax, at least one filler and at least one additive.

According to preferred aspect of the invention, the applicator comprises an applicator head having two opposite faces, wherein the applicator head comprises:
a) a first part having at least one housing, and
b) a second part that is connected to the first part by a hinge and is at least partially and fixedly engaged in the housing of the first part,
wherein the first and second parts are both accessible from each of said faces of the applicator head.

The present invention relates to a cosmetic care system comprising:
1) at least one composition as described above; and
2) an applicator;
  wherein the applicator comprises an applicator head having two opposite faces, the applicator head comprising:
  a) a first part having at least one housing, and
  b) a second part that is connected to the first part by a hinge, is at least partially engaged in the housing of the first part, and contains the product to be applied so as to allow application of the cosmetic product on first use without the need for a reservoir separate from the applicator member.

As per invention, the inventive compositions are related but not limited to liquid compositions, such as lipsticks, liners, foundations, mascaras, eyeshadows, skin care compositions, sunscreens, skin repellants, deodorants, nail compositions.

Another embodiment of this invention pertains to the composition being free or substantially free or devoid of non-volatile solvents having at least one or more phenyl groups, such as described in US. Pat. No. 8,945,525, the entire content of which is hereby incorporated by the reference.

The present invention also relates to a kit for a nail care system comprising (1) at least one composition as described above; and (2) an applicator.

In another embodiment, the invention is a method of making up skin involving applying onto the skin the above disclosed compositions with the applicator.

As per another embodiment, this invention relates to a system of cosmetic compositions comprising the color coat composition as previously described, a top coat composition and at least one applicator.

Figure 1:
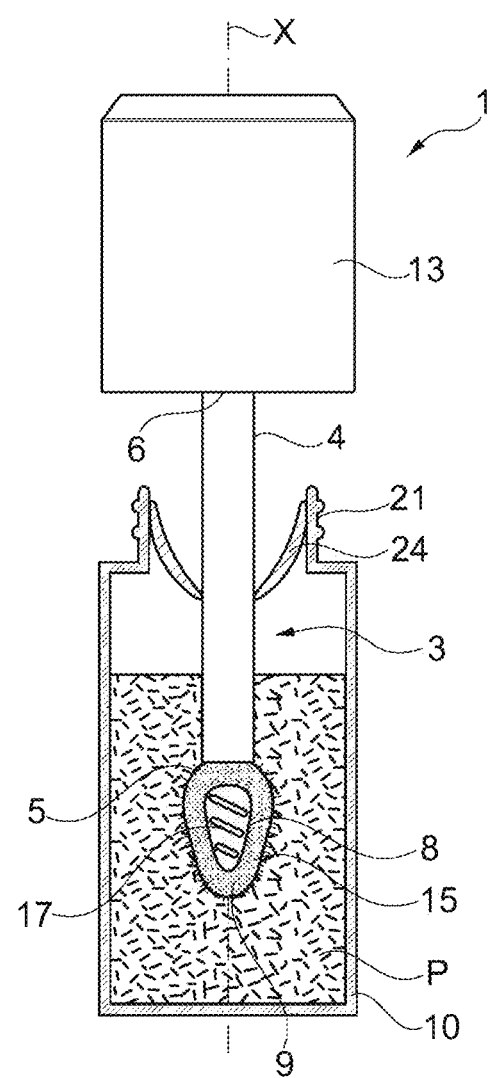
FIG. 1 shows an example of a packaging and application device according to the invention, FIG. 2 schematically illustrates an example of an applicator member according to the invention.

A—an oval applicator with two (2) openings in the central part, entirely cover with a flock B—a cone applicator entirely cover with a flock C—a bended cone applicator entirely cover with a flock D—a triangle applicator entirely cover with a flock E—a bended triangle applicator entirely cover with a flock F—Inventive applicator

DETAILED DESCRIPTION OF THE INVENTION

According to the invention, the term "anhydrous" refers to a composition not containing any water, that is to say a composition in which the water that may be present comes only from the water of crystallization or of adsorption of the starting materials. In any case, an anhydrous composition contains less than 5% by weight of water, preferably less than 1% by weight, and better still less than 0.5% by weight of water, relative to the total weight of the composition.

As used herein, the expression "at least one" means one or more and thus includes individual components as well as mixtures/combinations.

Other than in the operating examples, or where otherwise indicated, all numbers expressing quantities of ingredients and/or reaction conditions are to be understood as being modified in all instances by the term "about," meaning within 10% to 15% of the indicated number (e.g. "about 10%" means 9%-11% and "about 2%" means 1.8%-2.2%).

"Film former" or "film forming agent" or "film forming polymer or" "film forming resin" as used herein mean a polymer or resin that leaves a film on the substrate to which it is applied, for example, after a solvent accompanying the film former has evaporated, absorbed into and/or dissipated on the substrate.

"Transfer resistance" as used herein refers to the quality exhibited by compositions that are not readily removed by contact with another material, such as, for example, a glass, an item of clothing or the skin, for example, when eating or drinking. Transfer resistance may be evaluated by any method known in the art for evaluating such. For example, transfer resistance of a composition may be evaluated by a "kiss" test. The "kiss" test may involve application of the composition to human keratin material such as hair, skin or lips followed by nabbing a material, for example, a sheet of paper, against the hair, skin or lips after expiration of a certain amount of time following application, such as 2 minutes after application. Similarly, transfer resistance of a composition may be evaluated by the amount of product transferred from a wearer to any other substrate, such as transfer from the hair, skin or lips of an individual to a collar when putting on clothing after the expiration of a certain amount of time following application of the composition to the hair, skin or lips. The amount of composition transferred to the substrate (e.g., collar, or paper) may then be evaluated and compared. For example, a composition may be transfer resistant if a majority of the product is left on the wearer's hair, skin or lips. Further, the amount transferred may be compared with that transferred by other compositions, such as commercially available compositions. In a preferred embodiment of the present invention, little or no composition is transferred to the substrate from the hair, skin or lips.

"Long wear" compositions as used herein, refers to compositions where color remains the same or substantially the same as at the time of application, as viewed by the naked eye, after an extended period of time. Long wear properties may be evaluated by any method known in the art for evaluating such properties. For example, long wear may be evaluated by a test involving the application of a composition to human hair, skin or lips and evaluating the color of the composition after an extended period of time. For example, the color of a composition may be evaluated immediately following application to hair, skin or lips and these characteristics may then be re-evaluated and compared after a certain amount of time. Further, these characteristics may be evaluated with respect to other compositions, such as commercially available compositions. For lip compositions, "long wear" typically means the composition remains on the lips at least about 4 hours up to about 24 hours, and retains rich color even after eating.

"Liquid" or "liquid cosmetic" or "liquid lipstick" or "liquoid composition" means a composition having a fixed volume, flows to cover the bottom and assumes the shape of the portion of the container it fills and is slightly compressible (as disclosed in *General chemistry,* Fourth Edition 2005, p.434

"Tackiness" as used herein refers to the adhesion between two substances. For example, the more tackiness there is between two substances, the more adhesion there is between the substances. To quantify "tackiness," it is useful to determine the "work of adhesion" as defined by IUPAC associated with the two substances. Generally speaking, the work of adhesion measures the amount of work necessary to separate two substances. Thus, the greater the work of adhesion associated with two substances, the greater the adhesion there is between the substances, meaning the greater the tackiness is between the two substances.

Work of adhesion and, thus, tackiness, can be quantified using acceptable techniques and methods generally used to measure adhesion and the one far along described.

"Substituted" as used herein, means comprising at least one substituent. Non-limiting examples of substituents include atoms, such as oxygen atoms and nitrogen atoms, as well as functional groups, such as amine groups, ether groups, alkoxy groups, acyloxyalky groups, oxyalkylene groups, polyoxyalkylene groups, carboxylic acid groups, amine groups, acylamino groups, amide groups, halogen containing groups, ester groups, thiol groups, sulphonate groups, thiosuiphategroups, siloxane groups, and polysiloxane groups. The substituent(s) may be further substituted.

"Comprising" it is meant that other steps and/or ingredients which do not affect the end result may be added. The products, compositions, methods and processes of the present invention can include all the essential elements and limitations of the invention described herein as well as any of the additional or optional ingredients, components, steps, or limitations described herein.

"Free" or "substantially free" or "devoid of" as it is used herein means that while it is preferred that no amount of the specific component be present in the composition, it is possible to have very small amounts of it in the compositions of the invention provided that these amounts do not materially affect at least one, preferably most, of the advantageous properties of the conditioning compositions of the invention. Thus, for example, "free of phenylated solvents" means that non-volatile solvents are preferably omitted (that is 0% by weight), but can be present in the composition at an amount of less than about 0.25% by weight, typically less than about 0.1% by weight, typically less than about 0.05% by weight, based on the total weight of the composition as a whole.

As used herein, all ranges provided are meant to include every specific range within, and combination of subranges between, the given ranges. Thus, a range from 1-5, includes specifically 1, 2, 3, 4 and 5, as well as subranges such as and 2-5, 3-5, 2-3, 2-4, 1-4, etc.

As used herein a range of ratios is meant to include every specific ratio within, and combination of subranges between the given ranges.

The compositions and methods of the present invention can comprise, consist of, or consist essentially of the essential elements and limitations of the invention described herein, as well as any additional or optional ingredients, components, or limitations described herein or otherwise useful.

Applicator

In accordance with the present invention, an applicator for applying a cosmetic composition to the keratinous surface is provided. Preferably, the applicator is one as disclosed in WO2016046355 (PCT/EP2015/072069), the entire contents of which is herein incorporated by references.

The present invention relates to the application of a cosmetic product to human keratin materials, in particular the skin, the lips, or the eyelashes and/or eyebrows.

According to preferred embodiments, the applicator comprises an applicator head having two opposite faces, the applicator head comprising:
a first part having at least one housing, and
a second part that is connected to the first part by a hinge and
  is at least partially and fixedly engaged in the housing of
  the first part,
wherein the first and second parts are both accessible from
  each of said faces of the applicator head.

By "fixedly engaged", it should be understood that in an applicator according to the present invention, the second part of the applicator head remains engaged in the housing of the first part and is not easily movable relative to the latter. No external force for example exerted by a user or by a collar of a reservoir into which the applicator head is inserted is needed for maintaining the engagement.

The applicator head can have a flattened overall shape and said faces can correspond to the main faces.

The invention affords new possibilities for producing the applicator member, with different surface states and/or different materials on the first and second parts. In particular, the invention makes it very easily possible for only one of the parts to be flocked, if so desired, or for them to he flocked differently. Such partial flocking, limited to one of the parts, also gives the applicator an attractive appearance.

The expression "are both accessible from each of said faces of the applicator head" is understood as meaning that, on each of these faces, the first and second parts are at least partially present at the surface and/or accessible through a through-opening. This can make it possible, if desired, to produce the applicator member such that, during the application of the cosmetic product from one of said faces, the human keratin materials come into contact with at least one of the first and second parts, better still into contact with both if the user so desires.

Along at least a portion of the length of the applicator member, it is possible for both portions to be visible on each of said faces; in a variant, along at least a portion of the length of the applicator member, only one of the parts is visible on one of said faces. This is the case, for example, when the first part has a housing in the form of a slot in which an upper portion of the second part bearing spikes is engaged, the second part comprising a lower part that defines a shoulder at the base of the upper portion, and when the first part is set back from the edge of this shoulder.

The body of the applicator member can be produced in one piece, by moulding thermoplastic material(s).

Preferably, the housing in the first part is a through-housing, thereby allowing access to the second part from each of said faces of the applicator head.

The second part can contain the product to be applied. It can thus comprise, on at least one of said faces, a cavity containing the cosmetic product to be applied. Preferably, the cavity is different from spaces formed between adjacent bristles or teeth present on an applicator. This product is for example semi-solid, of the rouge or lip-gloss, foundation, mascara or eyeshadow type, and comes directly into contact with the keratin materials during the use of the applicator member.

The product contained in the cavity can be in the form of a poured or compacted mass of product, without impregnation of a porous structure. In a variant, the mass of product impregnates a porous structure.

Thus, in a variant, the second part comprises, on at least one of said faces, a porous material which can be impregnated with the cosmetic product prior to being used for the first time, or in a variant, be impregnated with product during first use.

The possibility of producing the applicator member, if desired, with product contained therein without the latter having to be taken up makes it possible to reduce the bulkiness of the device and to make it easier to use.

In a variant, the user makes use of a reservoir of product and the applicator member belongs, for example, to an applicator designed to close this container when not in use.

Preferably, the abovementioned hinge is disposed on the applicator member away from the distal end of the applicator head. The hinge is preferably a film hinge or comprises two flexible strands. The hinge can be moulded with the body of the applicator member from a thermoplastic material.

At least one of the first and the second part, preferably the first part, is at least partially, better still entirely, flocked. The flocking bristles allow better retention of the cosmetic product on the applicator member and make it easier to spread it over the area to be treated. Preferably, the other of the first and the second part, in particular the second part, is not flocked. This makes it possible, if desired, to limit the quantity of cosmetic product that collects on the applicator member.

This other part can be produced without a cavity forming a reservoir.

One or more reliefs can be produced on this other part in order to exert for example a massaging action on the skin or the lips or to separate the eyelashes or eyebrows.

In a variant, this other part is at least partially flocked, but the flocking of the first part can be different from the flocking of the second part, in particular in terms of quantity of fibres, sizes of fibres and/or physical properties of the fibres, for example stiffness of the fibres.

Two different flockings can make it possible to have different effects during the application of the cosmetic product. In addition, attractive aesthetic effects can be obtained, by using for example different colours for the fibres.

At least one of the first and second parts, preferably the second part, can have protruding or recessed reliefs, for example in the form of spikes, bosses, ridges, grooves, or cavities, in particular in a regular arrangement. Advantageously, the first part is flocked and the second part comprises recessed or protruding reliefs, for example in the form of spikes. The presence of spikes can make it possible to separate the eyelashes and/or eyebrows during the application of product to the latter.

The first part can bear a flocked coating and the second part spikes, or vice versa, in particular one or more rows of longitudinally extending spikes.

The protruding reliefs can also be produced so as to make it possible to bring out a massaging effect on the skin or this lips during the application of the cosmetic product. The recessed reliefs can promote the accumulation of product on the applicator member and enhance the autonomy thereof.

The second part can protrude upwardly and/or downwardly from the first part when the applicator member is viewed from the side in the horizontal state. It can be smooth and have overall shape that protrudes upwardly and downwardly from the first part, being for example in the form of a ball having a diameter greater than the thickness of the first part. The expression "side view" denotes a view perpendicularly to a median plane for said faces, this median plane being substantially perpendicular to the flattening plane of the applicator head.

The second part may bear a pattern or an inscription in the form of a relief or printing.

The second part may take up all of the housing of the first part. In a variant, the second part only takes up some of the housing of the first part, the first and the second part defining a space between one another for product to collect in. This space is filled for example with product when the applicator member is dipped into a container containing the product.

The second part may be engaged entirely in the corresponding housing of the first part.

The first part may be produced with two arms that meet at their ends and define between one another the housing in which the second part is engaged.

When one of said faces is viewed from the front, the first part can extend all around the second part. The first part can bear a flocked coating all around the second part.

The applicator head can have a width which decreases, in front view, in the direction of its free end.

The two arms of the second part can converge towards one another in the direction of the distal free edge.

The applicator head can have, in side view, a thickness which varies relatively little in the direction of the distal free edge, in particular which varies by less than 25% from a thickness at a given location, along 90% of its length.

The contour of the second part may be rounded both in cross section and when it is viewed from the front.

The second part may be engaged partially in the housing of the first part and not entirely; for example a fixing tab of the second part is engaged in the housing of the first part. The first part then surrounds the second part at least partially, better still entirely.

The second part can comprise a through-opening through which the first part is accessible. When one of said faces is viewed from the front, the visible surface of the second part can surround the visible surface of the first part at least partially, better still entirely. When the other of said faces is viewed from the front, the visible surface of the first part can surround the visible surface of the second part at least partially, better still entirely.

Preferably, the first part is made of a flexible material, in particular elastomer.

The first and the second part preferably form a single part moulded in thermoplastic material.

Preferably, the applicator head is attached to a mounting or gripping end piece of the applicator member. The end piece is preferably formed from two half end pieces that are connected together by the abovementioned hinge. Preferably, this hinge is disposed at the end of the end piece away from the applicator head. The two half end pieces can be flapped together to form the complete end piece, serving for example to be mounted in an applicator stem.

The applicator member may comprise an end piece substantially in the form of a cylinder of revolution, formed by two half end pieces; each half end piece can be attached to one of said parts by a flared transition zone that widens in the direction of the corresponding part.

A portion of the applicator member can be overmoulded on the rest of the applicator, in particular in a different material.

The applicator head can extend with its longitudinal axis aligned with that of the end piece. In a variant, the longitudinal axis of the applicator head forms a non-zero angle with that of the end piece.

The first and the second part can be fixed together in the use configuration, so as to be easily disassemblable or not, by snap-fastening or force-fitting. The second part may comprise a protruding relief at its periphery, said protruding relief cooperating with a recessed relief on the first part, or vice versa. In a variant, the two half end pieces or the first and second parts comprise other cooperating reliefs that make it possible to keep the first and second parts in the use configuration.

The first part may comprise a fixing hook and/or the second part may comprise a fixing tab, the fixing hook being inserted into or under the through-opening in the second part and the fixing tab engaging in the housing of the first part, the fixing tab cooperating with the fixing hook in order to keep the second part folded over the first part. Preferably, the fixing tab has a tooth which, during the folding of the second part over the first part, engages with the fixing hook by snap-fastening.

Preferably, one of the fixing hook and the fixing tab, in particular the fixing tab, is flush with the surface of one of the main faces.

In a further variant, the first and the second part are not fixed together but only folded together. The first and second parts are then held for example by the introduction of the end piece of the applicator member into a recess in a stem, the end piece fitting for example tightly in the recess or the stem being crimped by the end piece, such that the two half end pieces, and as a result the first and the second part, are kept pressed together.

In one way or another, the second part remains fixedly engaged in the housing of the first part.

A further subject of the invention, according to another of its aspects is thus an applicator member for applying a cosmetic product to human keratin materials, comprising an applicator head having two opposite faces, the applicator head comprising:
 a first part having at least one housing, and
 a second part that is connected to the first part by a hinge, is at least partially engaged in the housing of the first part, and contains the product to be applied so as to allow application of the cosmetic product on first use without the need for a reservoir separate from the applicator member.

Preferably, according to this second aspect of the invention, the first and second parts are both accessible from each of the main faces of the applicator head, as for the applicator member defined above.

According to a third aspect, a subject of the invention is an applicator member for applying a cosmetic product to the lips, comprising an applicator head having:
 a first part having at least one housing, and
 a second part that is connected to the first part by a hinge and is at least partially engaged in the housing of the first part, the second part comprising spikes, the first part comprising a flocked coating.

The applicator head may have a face onto which the housing opens, the flocked coating extending for example all around the opening of the housing or along the housing, on one side or both sides thereof.

A further subject of the invention, according to another of its aspects, is a device for applying a product to human keratin materials, comprising:
 a stem,
 an applicator member according to the invention, according to the first or the second aspect as defined above, the applicator member being fixed to the end of the stem.

The end piece of the applicator member is preferably inserted into an open recess at the end of the stem.

Preferably, the device comprises a container containing the cosmetic product to be applied. This container may comprise a wiping member.

The device can serve for the application of the product to the skin, including the lips. In a variant, the device is configured for the application of the product to the eyelashes and/or eyebrows.

The container may contain make up or care products to be applied to the keratinous substrate, in particular a foundation, an eyeshadow, a concealer product, a complexion corrector, a lipstick, or a lip gloss, or a product to be applied to the eyelashes and/or eyebrows, in particular mascara.

A further subject of the invention, according to another of its aspects, is a method for manufacturing an applicator member according to the invention, comprising the steps of:
 molding a body of the applicator member in the open state, comprising
  a first part having at least one housing, and
  a second part that is connected to the first part by a hinge and is intended to be engaged in the housing after the second part has been folded over the first part
 applying an adhesive to one of the first and the second part, preferably to the first part,
 applying flocking bristles to the adhesive,
 folding the second part over the first part so that the second part is at least partially engaged in the housing of the first part.

Preferably, the body of the applicator member comprises two half end pieces that are attached at their distal ends to the first and the second part, respectively, and are connected together at their proximal ends by the hinge.

The second part can be fixed to the first part by snap-fastening or force-fitting. In a variant, the second part and the first part are only folded together and kept in this state by an additional means, for example a stem into which the end piece is inserted.

A further subject of the invention is a method for manufacturing a device according to the invention, comprising the step of fixing the applicator member as defined above to a stem, for example by insertion of the end piece into an open housing at the end of the stem.

The packaging and application device 1 illustrated in FIG. 1 comprises a container 10 containing a product P to be applied and an applicator 3 for taking up and applying the product contained in the container.

Figure 2:
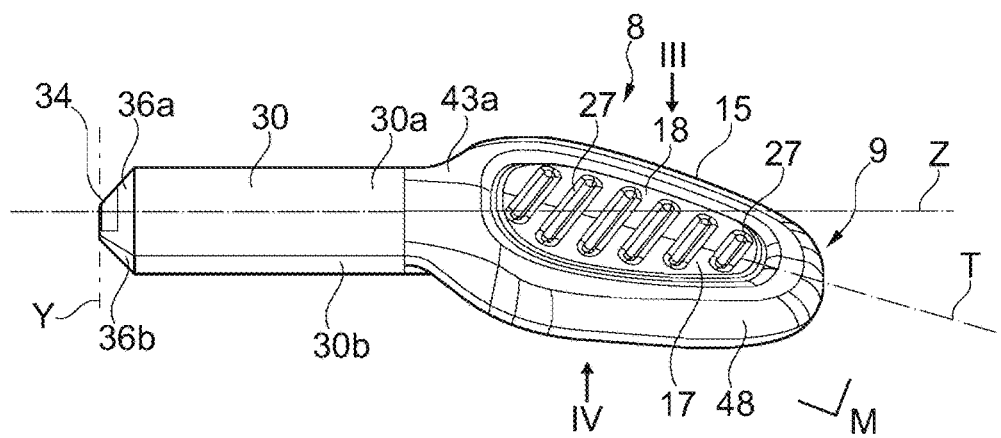
Figure 3:
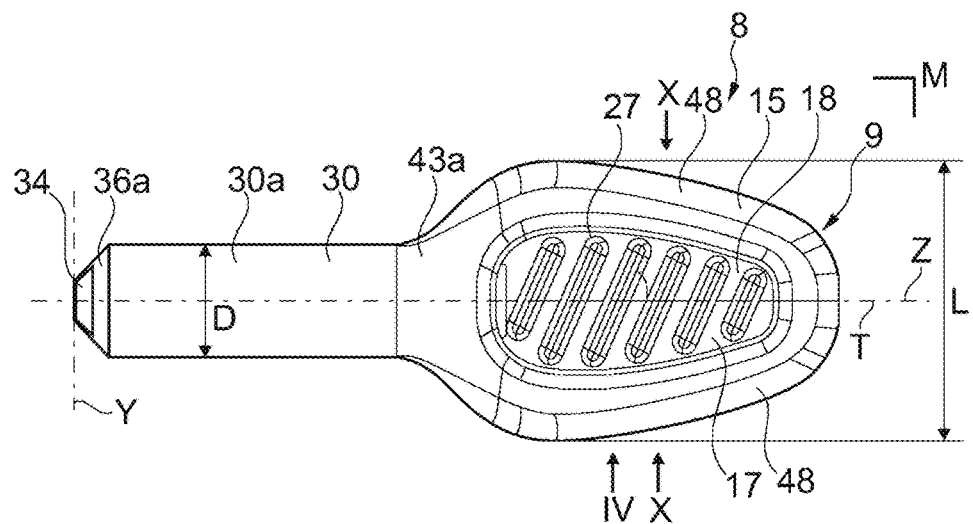
FIG. 3 shows a front view of the applicator member from FIG. 2, along III in FIG. 2.
Figure 4:
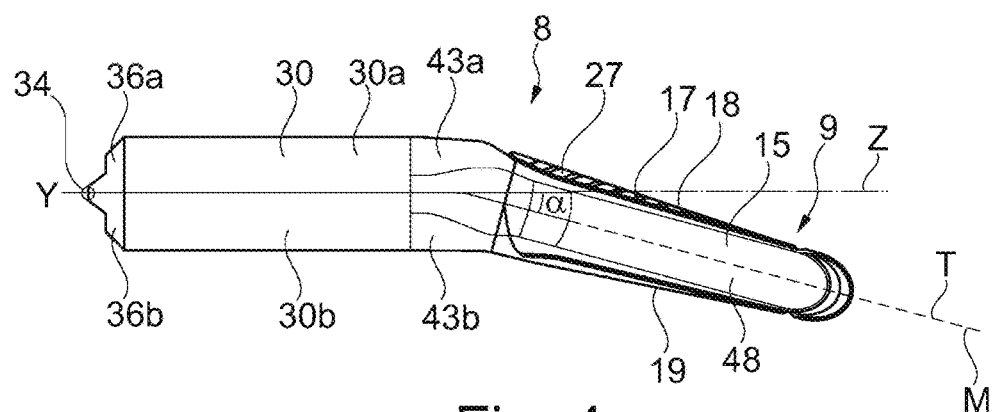
FIG. 4 shows a side view e applicator member from FIGS. 2 and 3, along IV in FIG. 2.

The applicator 3 comprises a stem 4 of longitudinal axis X, bearing at one 5 of its ends an applicator member 8 comprising an applicator head 9. As can be seen in FIGS. 2 to 4, the applicator head 9 comprises a first part 15 and a second part 17 that is engaged in the first part 15, these two parts being connected together by a hinge 34.

In the example illustrated, the axis X of the stem 4 is rectilinear, but it could be curved in a variant.

The container 10 may comprise in its upper part a neck 21, as illustrated. A wiping member 24 is engaged in this neck 21.

As illustrated in FIG. 1, the stem 4 is provided at its other end 6 with a gripping element 13 that also forms a cap for leaktight closure of the container 10.

The distal end 5 of the stem 4 has a recess which receives a mounting end piece 30 of the applicator member 8.

The applicator head 9 extends along a longitudinal axis T and is attached to the end piece 30. The latter is formed by two half end pieces 30a and 30b that are in contact with one another and connected together by the hinge 34.

The two half end pieces 30a and 30b are connected to the first part 15 and to the second part 17, respectively. The end piece 30 can be held in the stem 4 by any means, in particular by adhesive bonding, force-fitting, stapling, screw-fastening, crimping or snap-fastening.

Preferably, the two half end pieces 30a and 30b each have a flat face 31a and 31b, the latter coming into contact with one another over their entire surface area. In a variant, these faces comprise one or more reliefs that cooperate, for example by snap-fastening.

Figure 18:
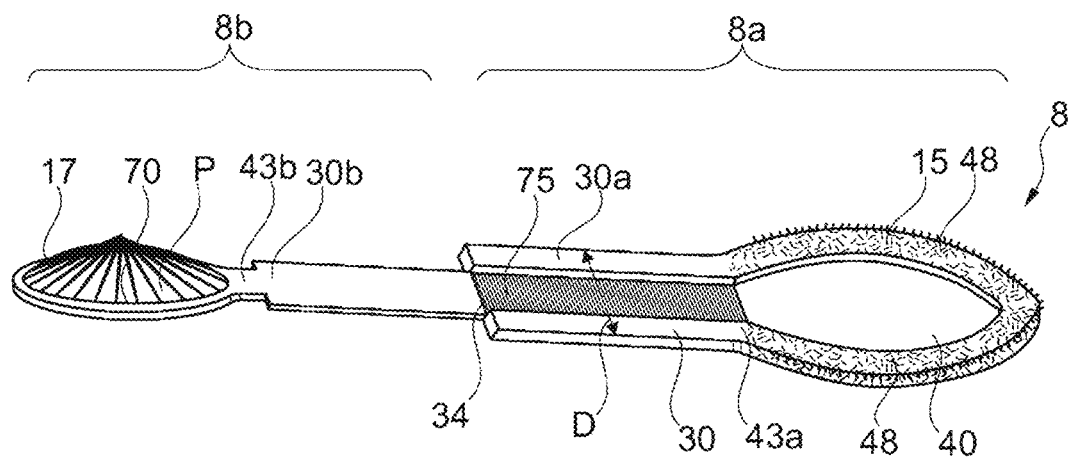

Thus, the possibility for one of the half end pieces 30a or 30b to comprise a recessed relief 75 for receiving the other half end piece has been illustrated in FIG. 18.

Preferably, the end piece 30 is in the form of a cylinder of revolution in the case of mounting in a stem. The end piece can be realized in a different manner, in particular when it is intended to serve directly for gripping.

Figure 5:
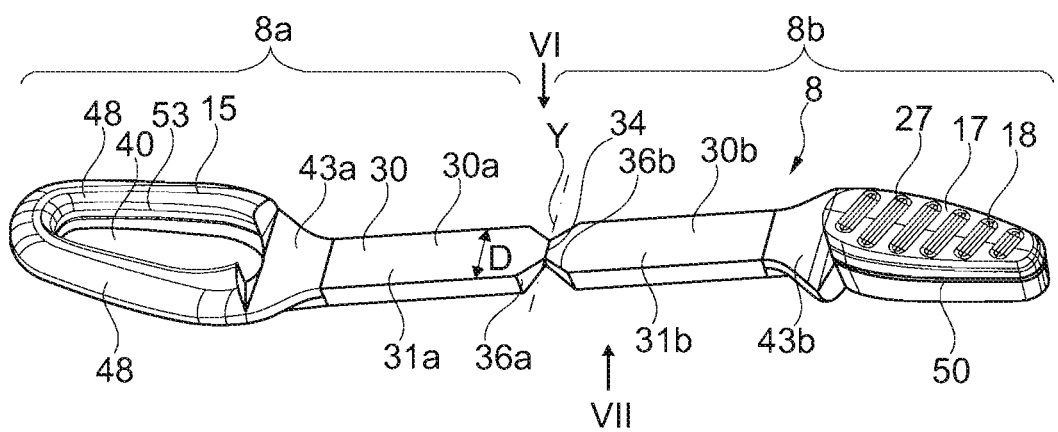
FIG. 5 shows the body of the applicator member from FIG. 2 in the open configuration.
Figure 6:
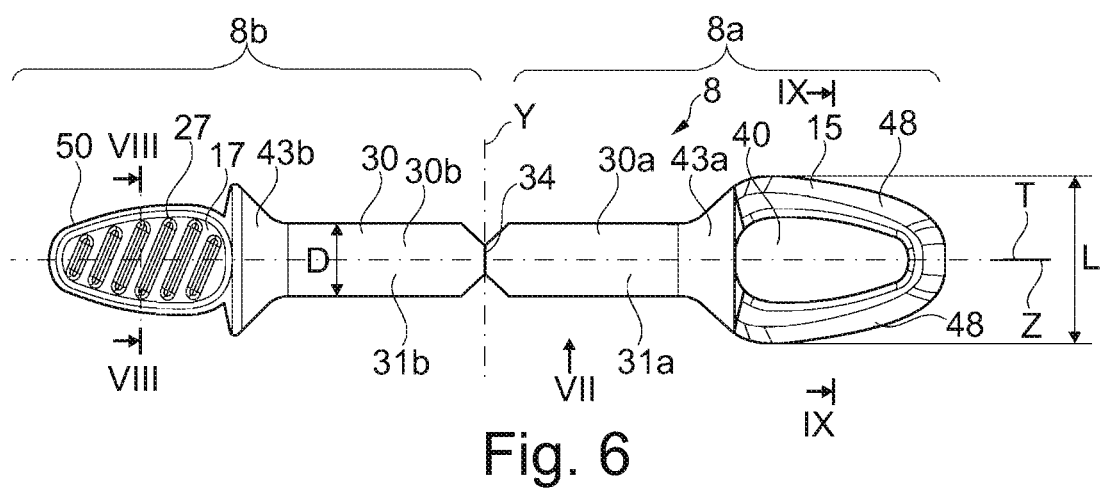
FIG. 6 illustrates a top view of the body of the applicator member from FIG. 5, along VI in FIG. 5.
Figure 7:
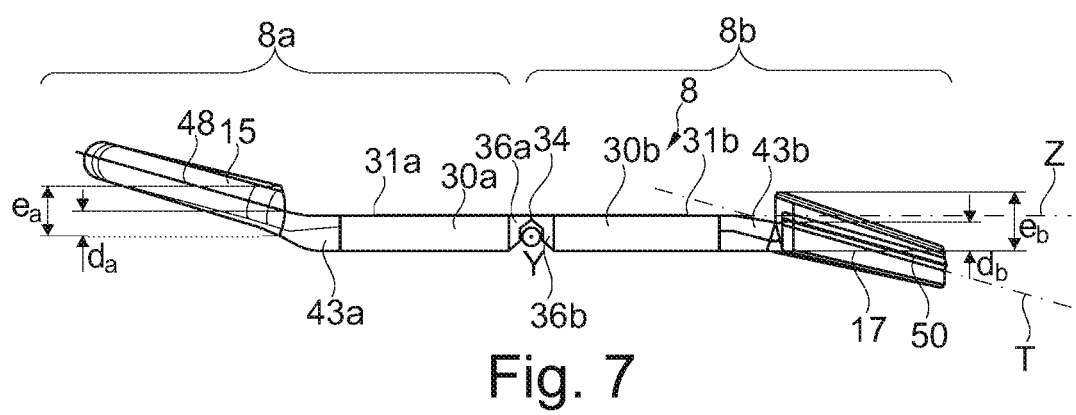
FIG. 7 shows a side view of the body of the applicator member from FIGS. 5 and 6, along VII in FIG. 6.

Preferably, the hinge 34 is disposed at those ends 36a and 36b of the two half end pieces 30a and 30b that are away from the first and second parts 15 and 17. It allows the two parts 15 and 17 and the two half end pieces 30a and 30b to be moulded in the open configuration in one piece and to be assembled by the second part 17 and the half end piece 30b being rotated about an axis Y of the hinge 34, perpendicular to the longitudinal axis Z of the end piece 30, as illustrated in FIGS. 5 to 7.

The applicator head 9 can be flatted overall in a plane M perpendicular to the plane of FIG. 4 and defines two opposite main faces 18 and 19. Preferably, the applicator head 9 has a greatest width L which is greater than that D of the end piece 30.

The first part 15 can be flocked, as illustrated in FIG. 1, and the second part 17 can comprise reliefs such as a plurality of ribs 27, as illustrated in FIG. 2. The ribs 27 extend preferably obliquely relative to the longitudinal axis T, forming an angle β with the longitudinal axis T.

The longitudinal axis T of the applicator head 9 preferably forms an angle α of preferably less than 45°, better still between 10 and 45°, with the longitudinal axis Z of the end piece 30.

As illustrated in FIGS. 5 to 7, the first and second parts 15 and 17 can each be attached to a respective half end piece 30a or 30b by way of a corresponding intermediate portion 43a or 43b which widens in the direction of the associated part. Preferably, the intermediate portions 43a and 43b are symmetrical such that when they are folded one over the other, the applicator member 8 has no discontinuities in its portion extending between the end piece 30 and the applicator head 9.

The hinge 34 is preferably a film hinge, as illustrated in FIGS. 5 to 7.

In the example in question, the first part 15 comprises two arms 48 that meet at their ends and define between one another a housing 40, in particular a through-housing, for receiving the second part 17. Preferably the first part 15 surrounds the second part 17 when the applicator member is viewed from the front, as in FIG. 3.

The housing 40 and the second part 17 have for example an approximately oval contour, as illustrated.

The second part 17 may entirely fill the housing 40.

The applicator head 9 can narrow slightly towards its free end, as illustrated in FIGS. 4 and 7.

Figure 8:
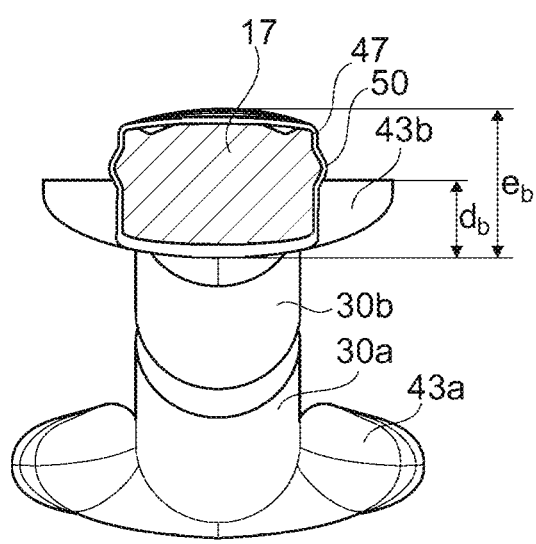
FIG. 8 is a cross section on VIII-VIII in FIG. 6.
Figure 9:
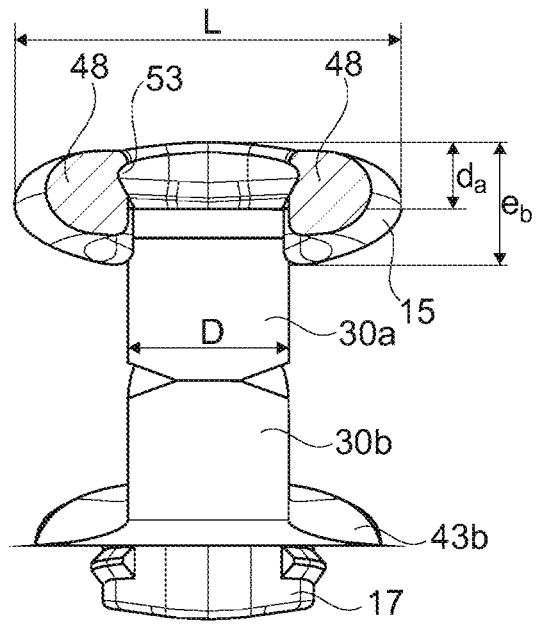
FIG. 9 is a cross section on IX-IX in FIG. 6.

As can be seen in particular in FIGS. 8 and 9, the first and second parts 15 and 17 can have respective thicknesses $e_a$ and $e_b$ which are greater than those $d_a$ and $d_b$ of the intermediate parts 43a and 43b.

Figure 10:
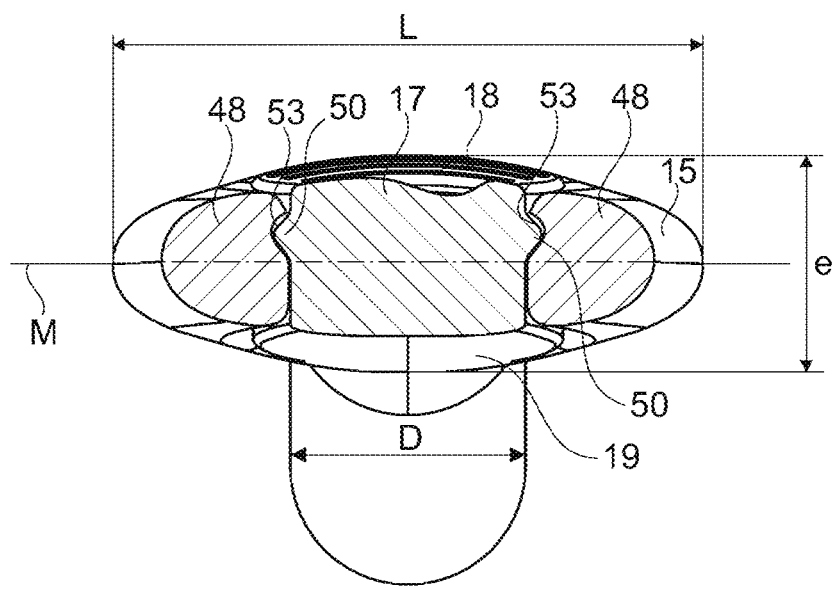
FIG. 10 is a cross section on X-X in FIG. 3, FIG. 11 schematically shows a perspective view of a variant embodiment of the applicator member according to the invention.

The total thickness e of the applicator head can be less than its greatest width L, as can be seen in FIG. 10.

As illustrated in FIG. 8, the second part 17 can have an approximately rectangular cross section and comprise a rib 50 at its periphery 47.

It can be seen in FIG. 9 that each arm 48 of the first part 15 can comprise a corresponding groove 53.

As illustrated in FIG. 10, the rib 50 is snap-fastened, during the folding the second part 17 over the first part 15, into the groove 53 in order to keep the applicator 8 in the closed position.

This does not have to be the case, and in particular the first part 15 can comprise a rib that is snap-fastened into a groove in the second part 17, or it is possible for the first and the second part 15 and 17 not to have any relief for snap-fastening.

FIGS. 11 to 17 show a variant embodiment of the invention, which differs from the one described with respect to FIGS. 1 to 10 mainly by the shape and size of the second part 17.

Figure 11:
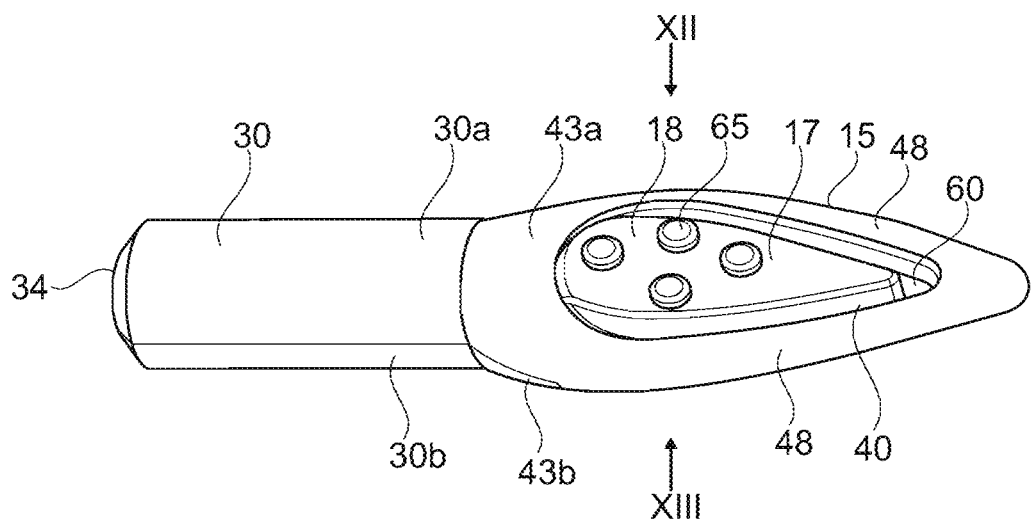
Figure 12:
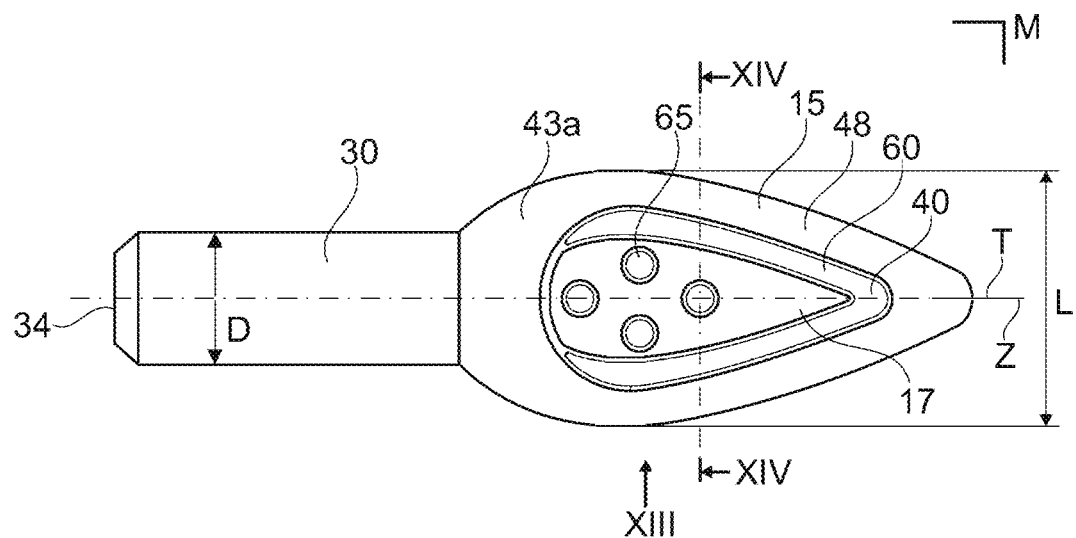
FIG. 12 illustrates a front view of the applicator member from FIG. 11, along XII in FIG. 11.
Figure 13:
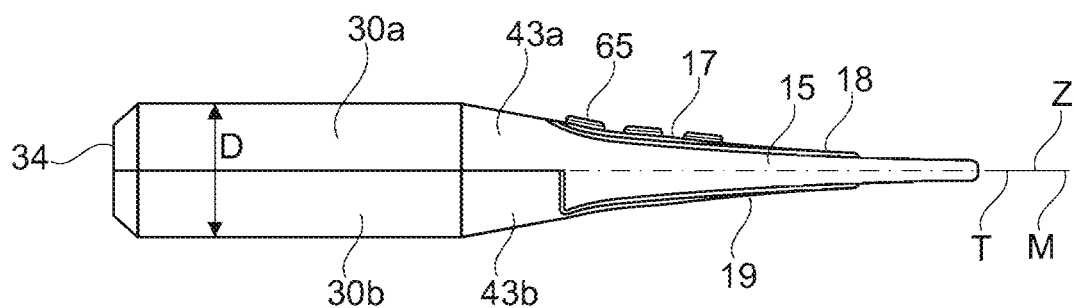
FIG. 13 shows a side view of the applicator member from FIGS. 11 and 12, along XIII in FIG. 11.
Figure 14:
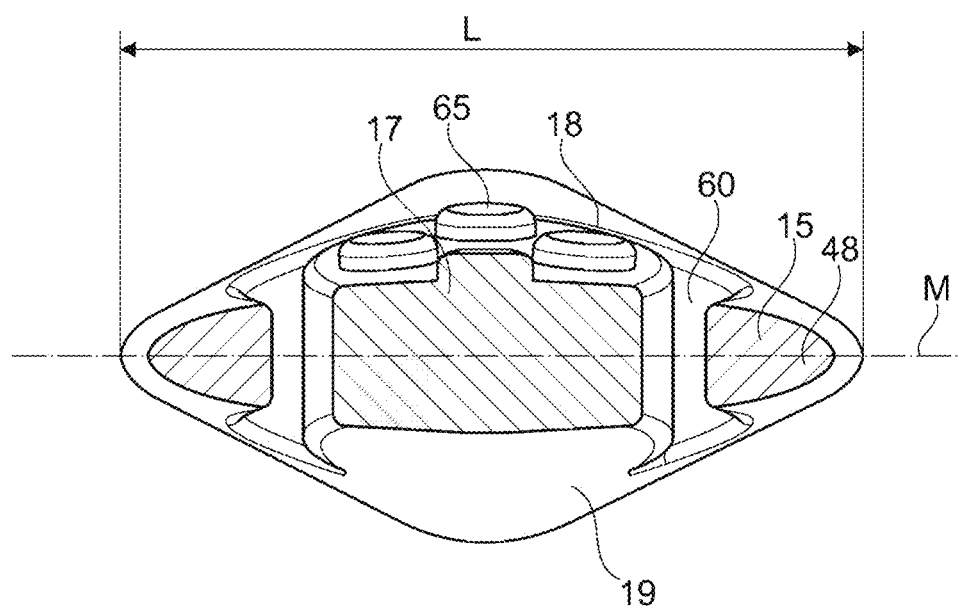
FIG. 14 is a cross section on XIV-XIV in FIG. 12.
Figure 15:
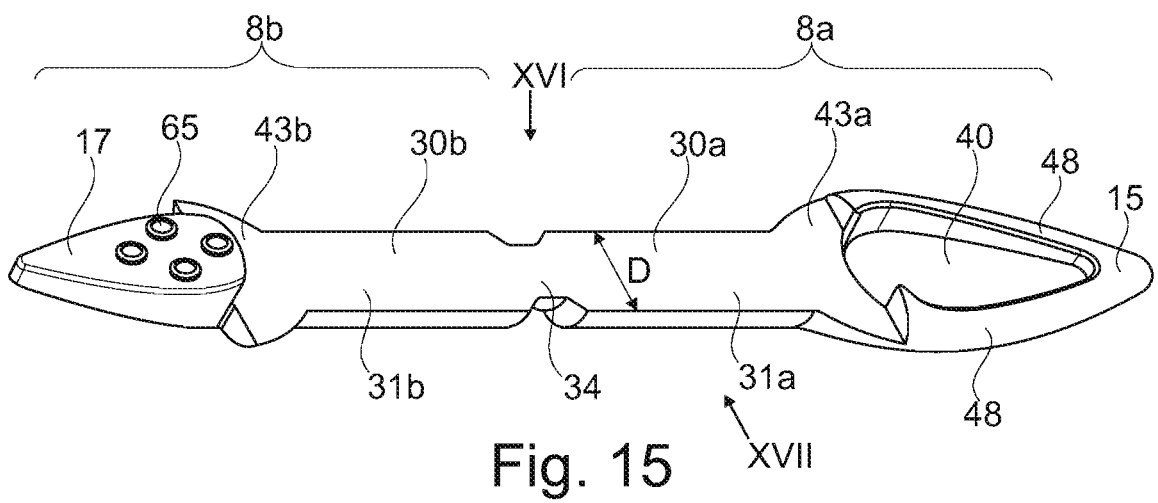
FIG. 15 shows the body of the applicator member from FIG. 11 in the open configuration.
Figure 16:
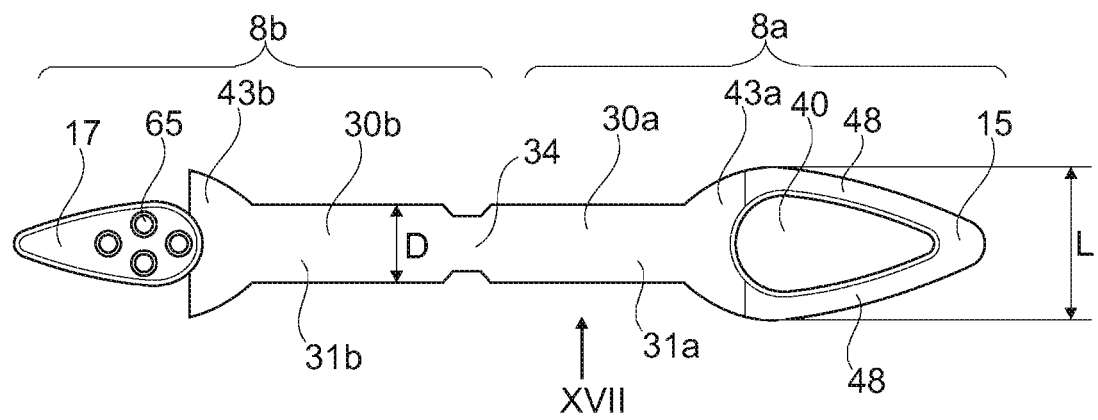
FIG. 16 is a top view along XVI in FIG. 15.
Figure 17:
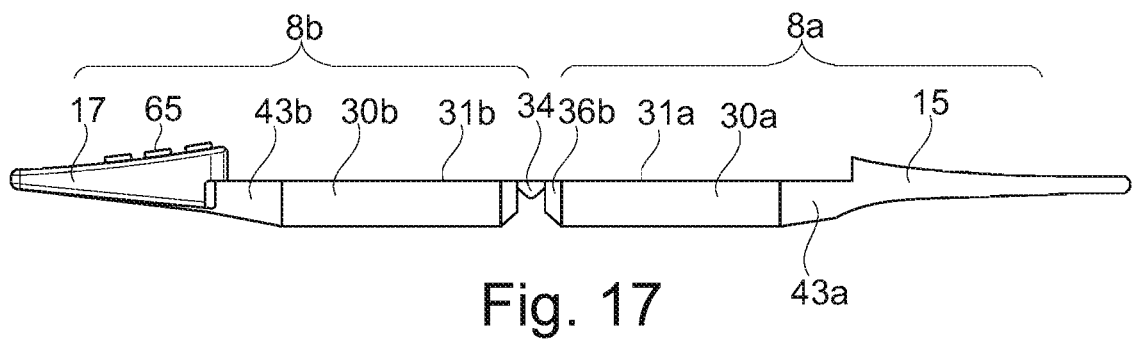
FIG. 17 is a side view along XVII in FIG. 16, FIG. 18 schematically illustrates a variant embodiment of the body of the applicator member, in the open configuration, FIG. 19 schematically and partially shows a front view of the applicator member from FIG. 18, following assembly.

As can be seen in FIGS. 11 to 13, the second part 17 can only partially fill the housing 40 such that a space 60 remains, in the applicator head 9, between the first part 15 and the second part 17, this allowing product to collect on the applicator head 9.

The second part 17 can have protruding reliefs 65, in particular bosses, in particular having a circular contour in front view, making it possible to exert a massaging action on the skin or the lips.

The two portions 8a and 8b can be kept in place by the insertion of the applicator member 8 into the recess in the stem 4. The two half end pieces 30a and 30b are then clamped together.

Figure 19:
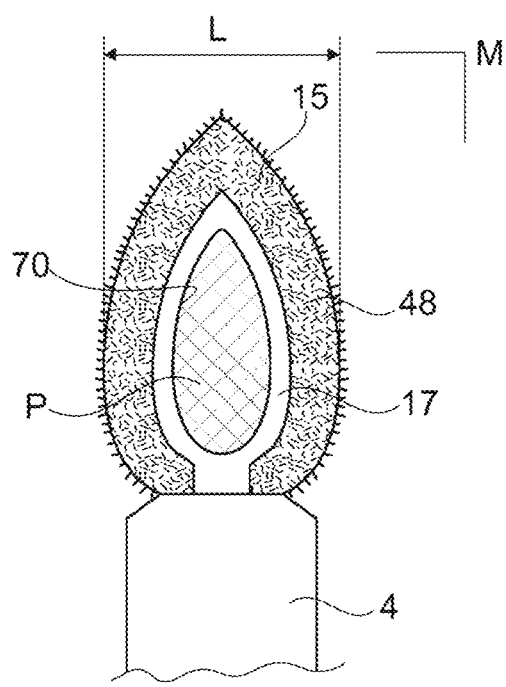

FIGS. 18 and 19 show a variant embodiment which differs from the example in FIGS. 1 to 10 by the shape of the second part 17.

The latter comprises a cavity 70, which is not a through-cavity, containing the cosmetic product P, which is thus only accessible from one side of the applicator member.

The cosmetic product P is for example of the eyeshadow, foundation, rouge or lip-gloss type, or mascara.

One of the half end pieces 30a and 30b can be wider than the other. For example, a recessed relief 75 extends along the half end piece 30a in order to receive the half end piece 30b.

Figures 20, 21, 22, 23:
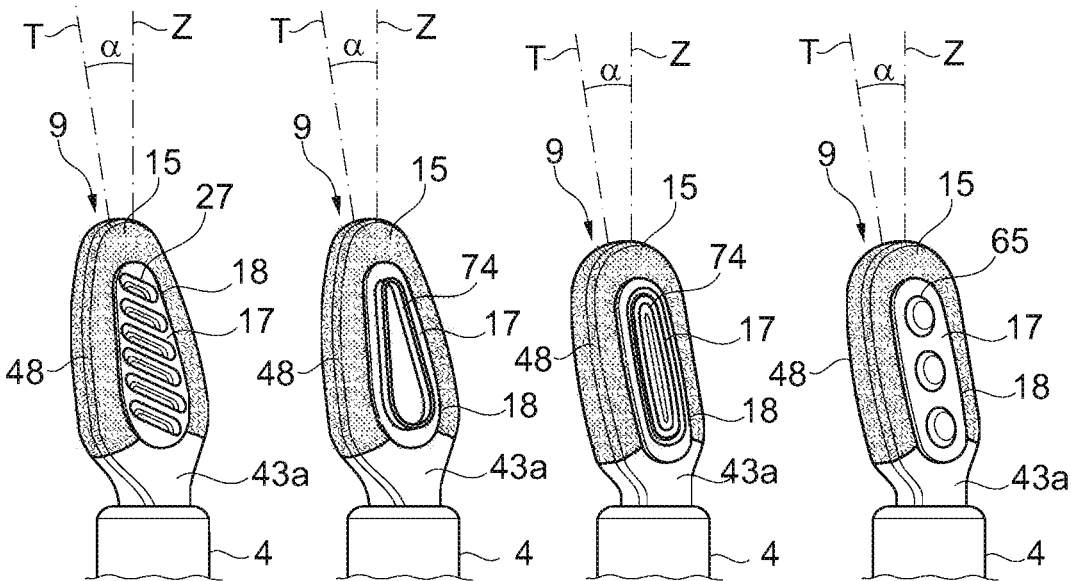
FIGS. 20 to 27 are schematic perspective views of variant embodiments of applicator members according to the invention.
Figures 24, 25, 26, 27:
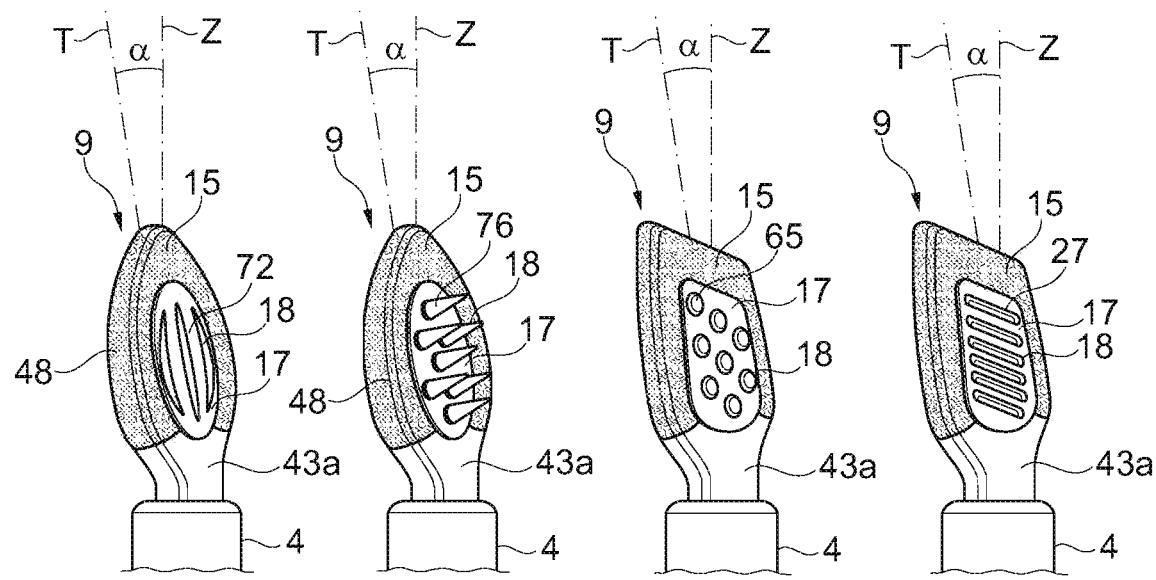

In the variants illustrated in FIGS. 20 to 27, the second part 17 comprises protruding or recessed reliefs of different shapes, in particular bosses 65, as illustrated in FIGS. 23, 25 and 26, oblique or transverse ridges 27, as illustrated in FIGS. 20 and 27, longitudinal grooves 72, as illustrated in FIG. 24, cavities 74, as illustrated in FIGS. 21 and 22, or spikes 76, as illustrated in FIG. 25.

When viewed from the front, the contour of the applicator head, along a major part of the length which is flocked, may be approximately elliptical, as illustrated in FIGS. 24 and 25, rectangular, as illustrated in FIGS. 26 and 27, have parallel side edges connected by a rounding, as in FIGS. 22 and 23, or have outwardly convex edges connected by a rounding, as in FIGS. 20 and 21.

Figure 28:
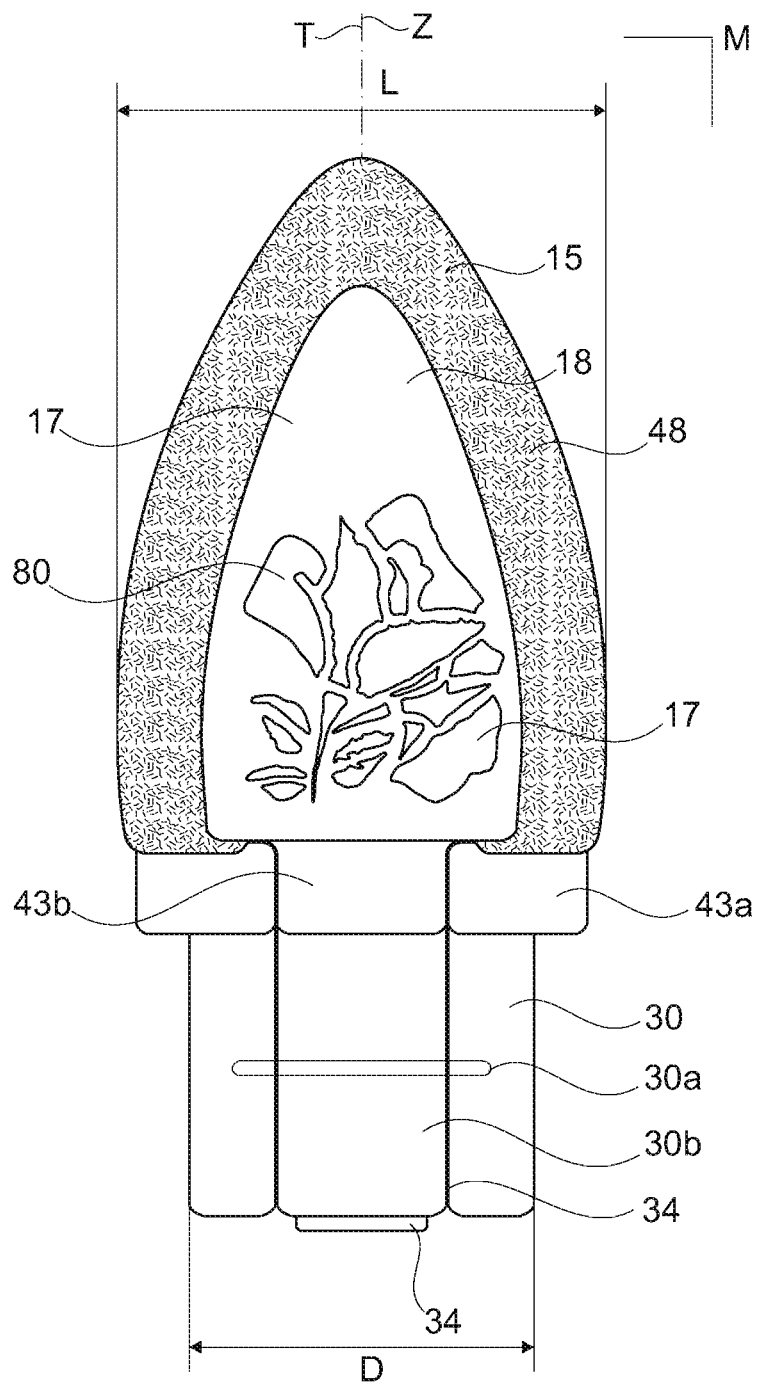
FIG. 28 shows a front view of another variant of an applicator member.

In the variant illustrated in FIG. 28, the second part 17 bears a relief 80 or an impression representing a decorative logo or an inscription that helps the user to get his/her bearings during use.

In the example in this figure, the end piece serves to be gripped directly by the user.

The end piece 30 can still be inserted into a covering element that serves as a gripping member. This embodiment makes it possible in particular to apply foundation.

Figure 29:
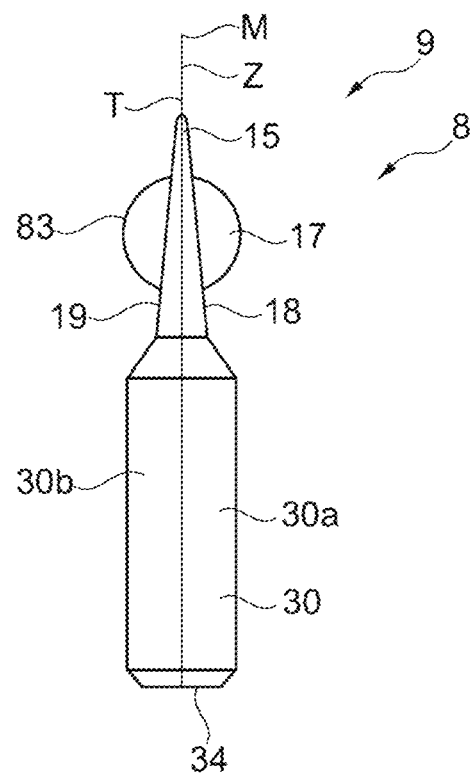
FIG. 29 shows a side view of another variant of an applicator member.
Figure 30:
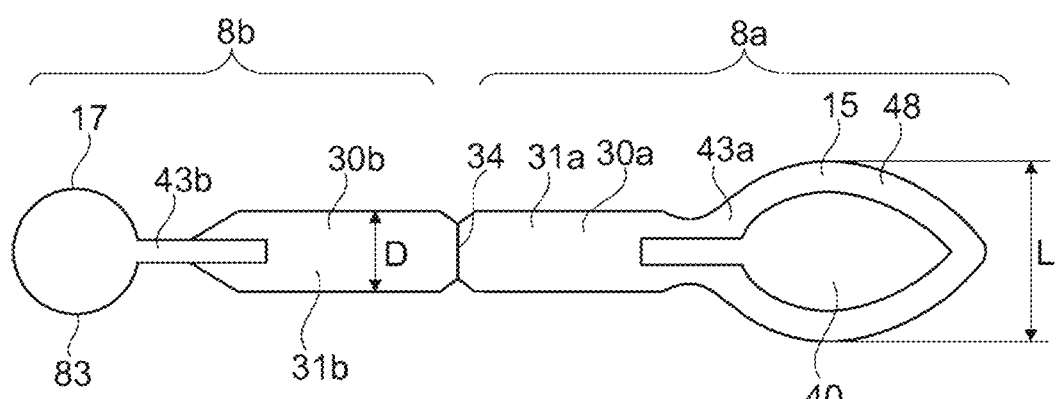
FIG. 30 shows the applicator member from FIG. 29 in the open configuration.
Figure 31:
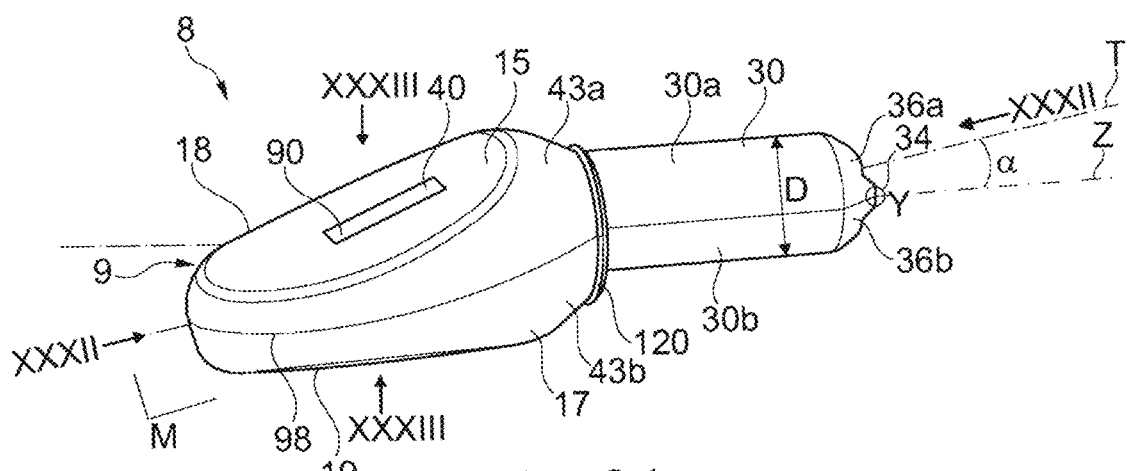
FIG. 31 is a schematic perspective view of a variant embodiment of an applicator member according to the invention.
Figure 32:
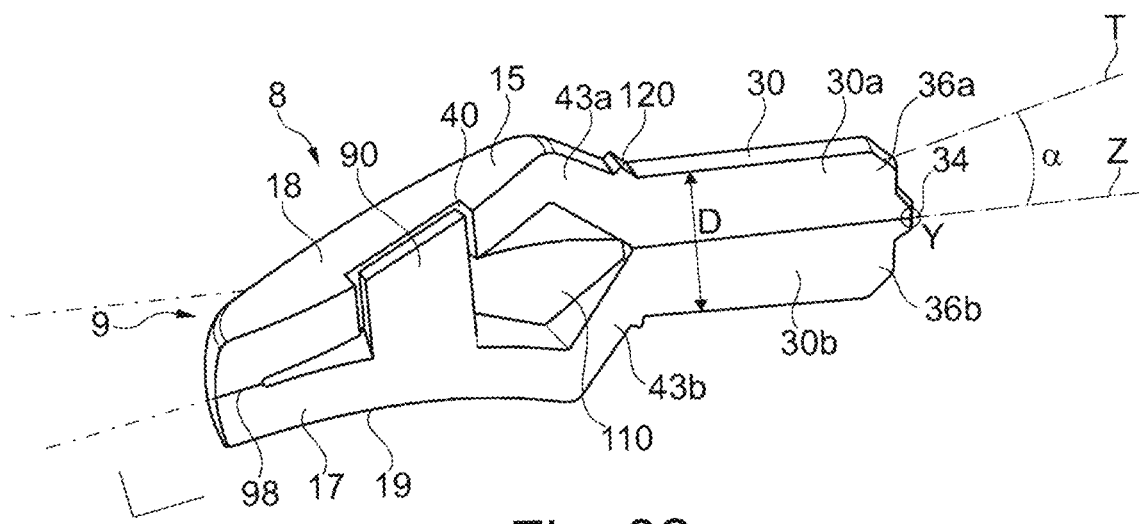
FIG. 32 is a longitudinal section on XXXII-XXXII in FIG. 31.

In the variant illustrated in FIGS. 29 and 30, the second part 17 is in the form of a bulge 83, for example in the form of a ball, which is housed in the housing 40 delimited by the first part 15 so as to protrude from both sides of the housing 40 in side view. This bulge 83 can make it possible to massage the keratin materials.

FIGS. 31 to 35 illustrate a variant embodiment of the invention, which differs from the one described with respect to FIGS. 1 to 10 mainly by the shape of the two parts and the manner in which they are fixed.

The first and second parts 15 and 17 have similar dimensions and, in the folded position, come into contact with one another.

Figure 33:
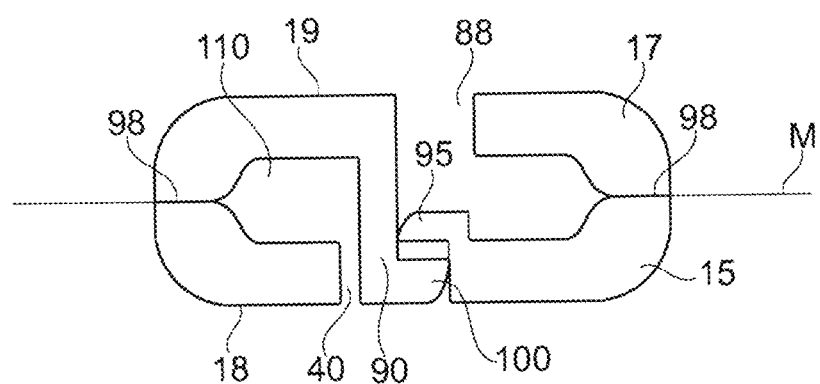
FIG. 33 is a cross section on XXXIII-XXXIII in FIG. 31.
Figure 34:
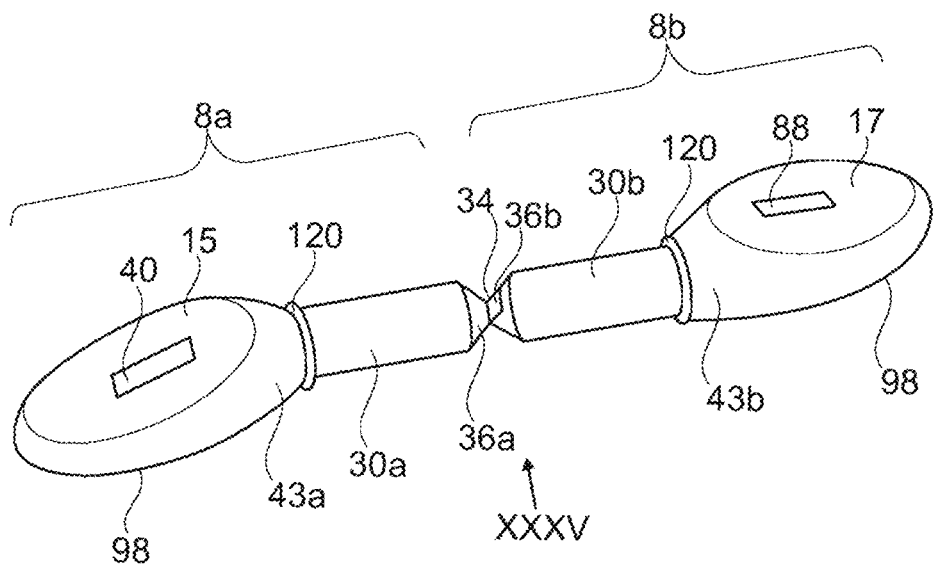
FIG. 34 shows the body of the applicator member from FIG. 31 in the open configuration.
Figure 35:
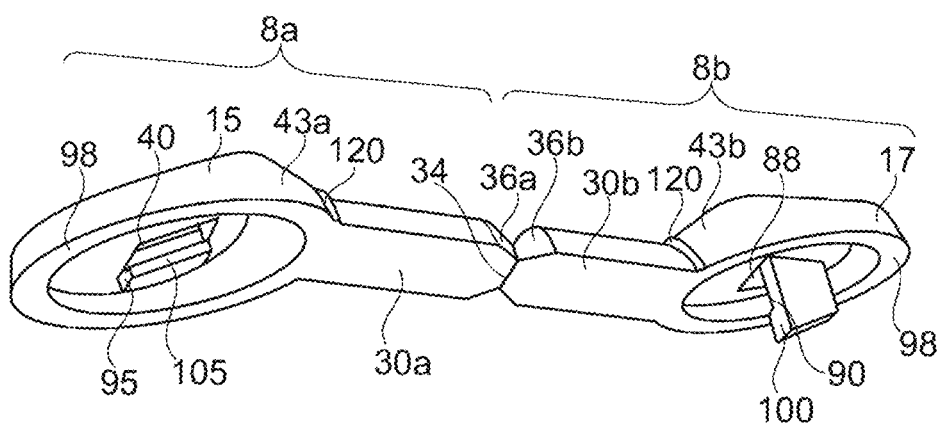
FIG. 35 shows a bottom view of the applicator member from FIG. 34, along XXXV.

The second part 17 comprises a through-opening 88, visible in FIG. 33 and a fixing tab 90 that is engaged in the housing 40. This fixing tab 90 has a tooth 100.

The first part 15 comprises a fixing hook 95 which, when the applicator member is in the folded position, is disposed in or under the through-opening 88 in the second part 17, such that it remains visibly accessible from the face 19. The fixing tab 90, in particular the tooth 100, and the hook 95 come into engagement with one another, as illustrated in FIG. 33.

In this example, the first and the second part 15 and 17 define, in the folded position, a free space 110 in the applicator head 9.

Preferably, as illustrated, the fixing tab 90 is flush with the face 8, such that, when the applicator member is used, the keratin materials can come into contact with its end.

As illustrated in FIGS. 31 to 35, the applicator member can comprise a flange 120 that serves as an end stop for insertion into the stem, this flange 120 being formed between the intermediate parts 43a and 43b and the half end pieces 30a and 30b.

FIGS. 36 to 59 show various examples of arrangements of the first 15 and second 17 parts of the applicator head in cross section.

In these figures, the residual clearance between the first and second parts may have been exaggerated for the sake of clarity.

Figure 36:
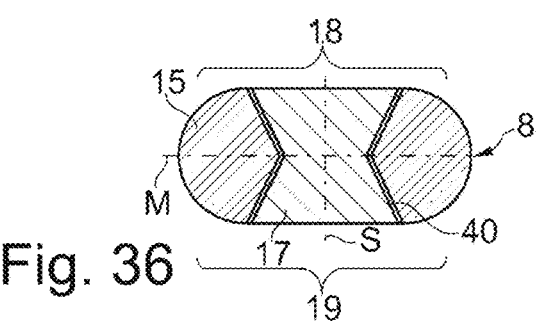
FIGS. 36 to 67 show variants of applicator members according to the invention in cross section, FIG. 68 schematically shows a perspective view of a mascara applicator produced in accordance with the invention.

In the example in FIG. 36, the applicator head has a flattened overall shape along a flattening plane M. As illustrated, the second part 17 has for example a cross section in the overall shape of an hourglass, which is held by complementing shapes in the housing 40 of the first part 15. The applicator part may have a symmetrical shape with respect to a plane of symmetry S which may be perpendicular to the flattening plane M.

Figure 37:
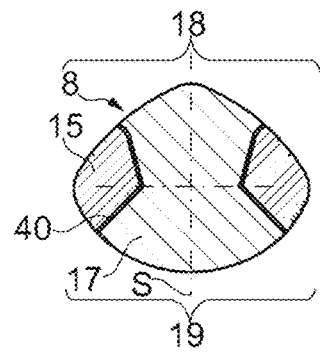

In the example in FIG. 37, the applicator head has the overall shape of an almond in cross section. The extents taken up by the second part on each of the opposite faces 18 and 19 of the applicator head may be different. In the example illustrated, the second part 17 thus takes up a smaller portion of the face 18 than of the face 19, the part 17 being wider at its base. The portion of the application surface that is defined by the second part 17 may have a smaller radius of curvature on the side of the face 18 than on the side of the face 19. In FIG. 37, the applicator head has a symmetrical shape with respect to the plane of symmetry S, but, in a variant that is not illustrated, the applicator head has an asymmetrical shape with respect to the median plane that intersects it half-way along its length.

As in the example in FIG. 36, the second part has a narrowing of its section between the faces 18 and 19, this keeping the second part in place in the housing 40. The plane in which the second part becomes narrowest may coincide, as illustrated, as the plane in which the first part 15 is at its widest. In the example in FIG. 37, the applicator head has a section which is asymmetrical with respect to a plane that intersects it half-way through its thickness.

Figure 38:
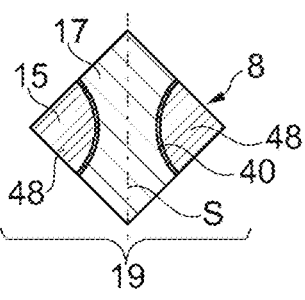

In the example in FIG. 38, the applicator head has a cross section which has a polygonal overall shape and more particularly, in the example in question, a square shape. The housing 40 in which the second part 17 is received may be defined between two arms 48 that have convex facing surfaces that are for example approximately in the form of a quarter circle. When the applicator head has a cross section with a polygonal overall shape, it can be symmetrical with respect to a median plane that intersects it half-way through its thickness, as illustrated. In a variant that is not illustrated, the applicator head has a cross section in the form of an irregular polygon.

Figure 39:
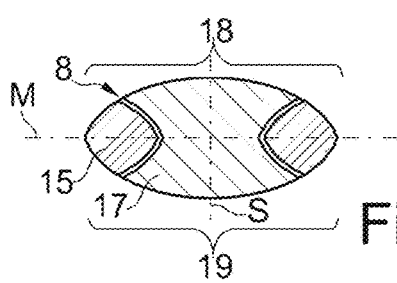

In the example in FIG. 39, the applicator head has a cross section which has an oval, for example elliptical, overall shape. The major axis of the section may be contained in a median plane M that intersects the applicator head half-way through its thickness. The applicator part may have a symmetrical overall shape with respect to a plane of symmetry S perpendicular to the median plane M.

Figure 40:
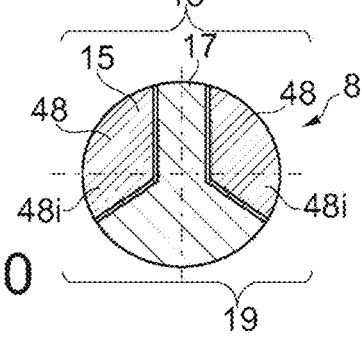

In the example in FIG. 40, the applicator head has a circular overall shape in cross section; it can be seen in this figure that the second part 17 can take up an area of the surface of each face 18 or 19 which is different depending on the face in question. Thus, in the example illustrated, the second part takes up a narrow central strip on the face 18 and virtually the entire face on the face 19, the rest of the latter being defined by the lower portions 48i of the arms 48.

Figure 41:
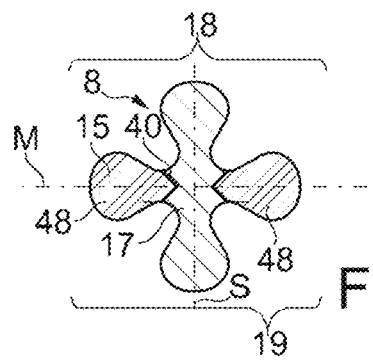

In the example in FIG. 41, the applicator head has a multilobe overall shape in cross section, with for example, as illustrated, four lobes. The housing 40 in which the second part 17 is received is defined between the arms 48 which constitute the left-hand and right-hand lobes. The applicator head can have a shape which is symmetrical with respect to a median plane M that intersects it half-way through its thickness and with respect to an orthogonal plane S.

Figure 42:
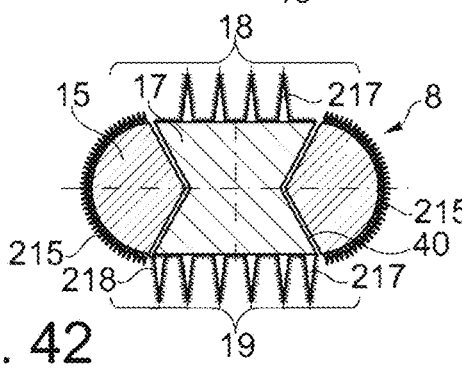

The variant embodiment in FIG. 42 differs from the one in FIG. 36 by way of the presence on the first part 15 of a coating of flocking fibres 215 and by the presence on the second part 17, on each of the faces 18 and 19, of spikes 217, the applicator being more particularly intended for making up the eyelashes and eyebrows. The number of spikes 217 and the disposition and/or shape thereof can differ between the faces 18 and 19; for example, as illustrated in FIG. 42, the number of spikes 217 on the face 18 is smaller than the number of spikes on the face 19.

Figure 43:
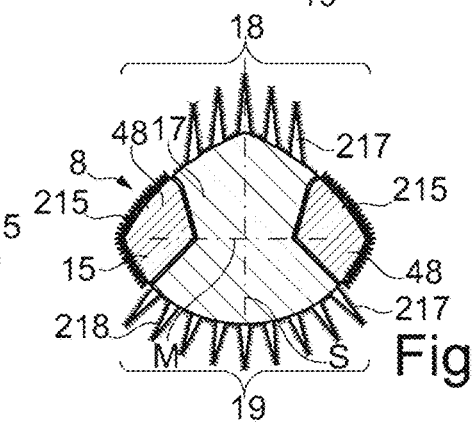

The exemplary embodiment in FIG. 43 differs from the one on in FIG. 37 essentially by presence of a coating of flocking 215 on the opposed faces of the arms 48 of the first part 15 and by the presence of spikes 217 on the second part 17, on the faces 18 and 19.

On the face 18, which corresponds to the upper side of the section in the figure, the spikes 217 are for example all aligned substantially parallel to the plane S, whereas on the face 19, the spikes 217 are oriented substantially radially.

It is also possible, as illustrated in FIGS. 42 and 43, to cover the spikes 217 with a flocked coating 218.

Figure 44:
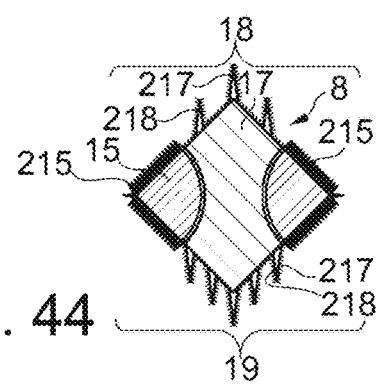
Figure 45:
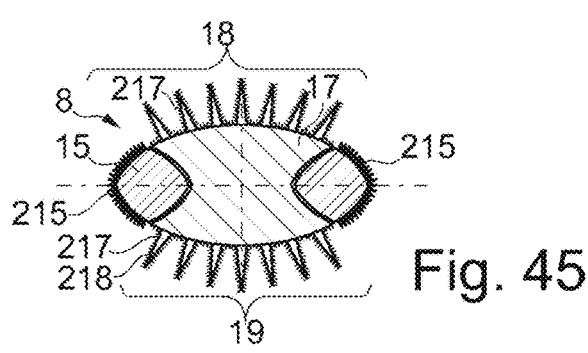

The same goes for the exemplary embodiments in FIGS. 44 and 45, which differ respectively from those in FIGS. 38 and 39 by the presence of the flocked coating 215, of the spikes 217 and of the flocked coating 218. In variants that are not illustrated, the flocked coating 218 is absent.

Figure 46:
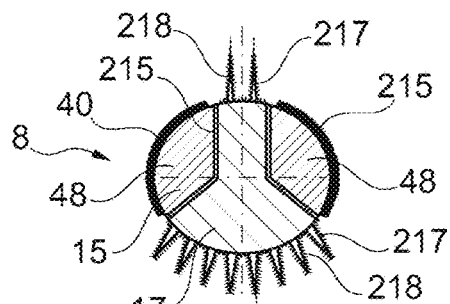
Figure 47:
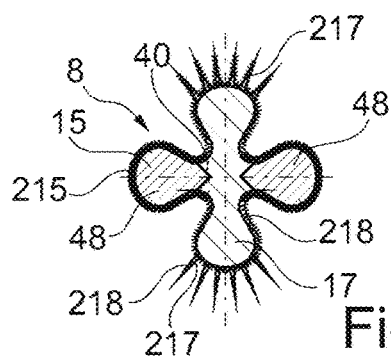
Figure 48:
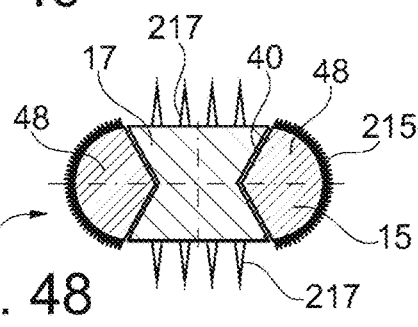
Figure 49:
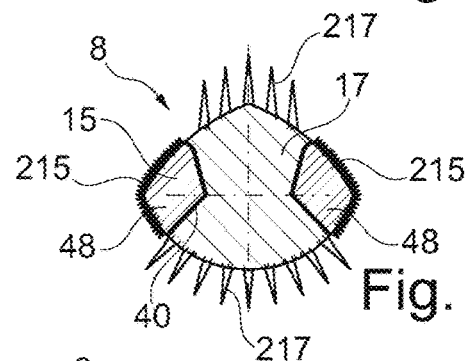
Figure 50:
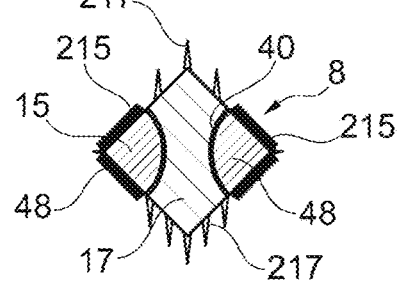
Figure 51:
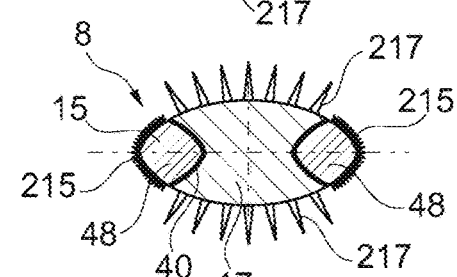
Figure 52:
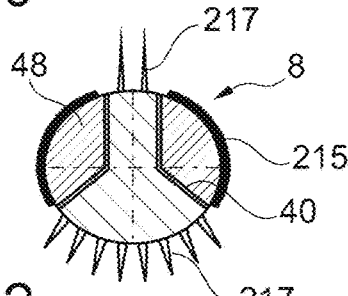
Figure 53:
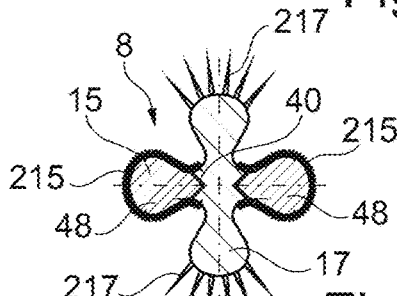
Figure 54:
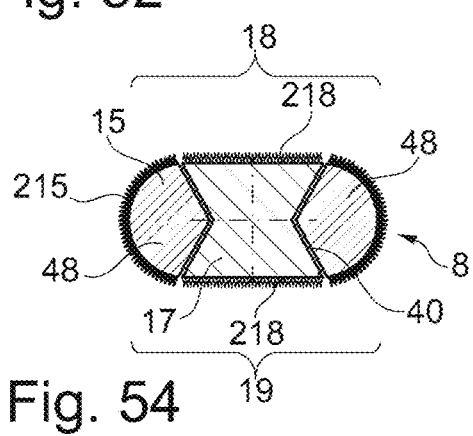
Figure 55:
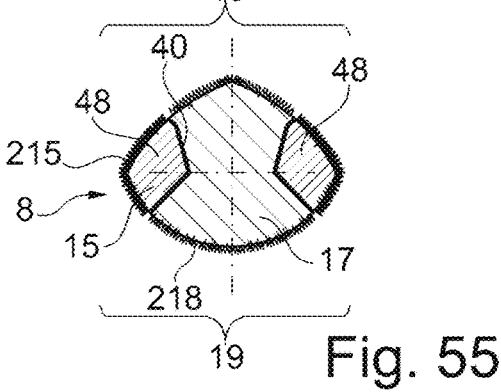
Figure 56:
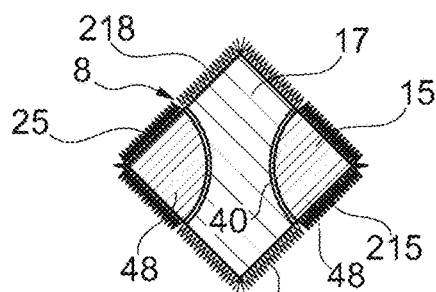
Figure 57:
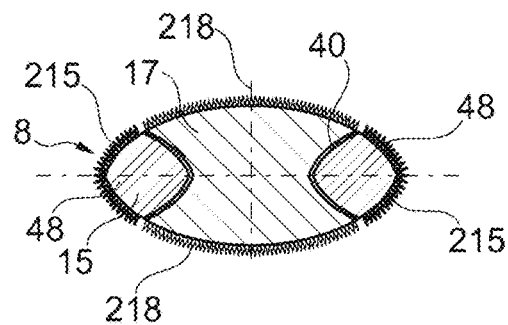
Figure 58:
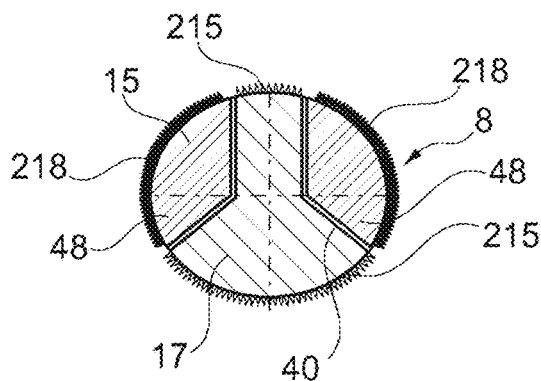
Figure 59:
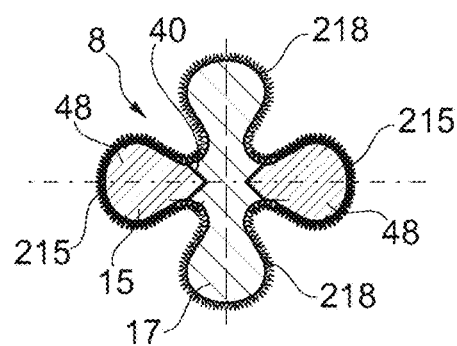
Figure 60:
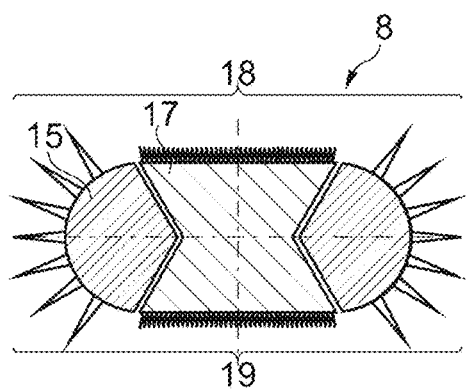
Figure 61:
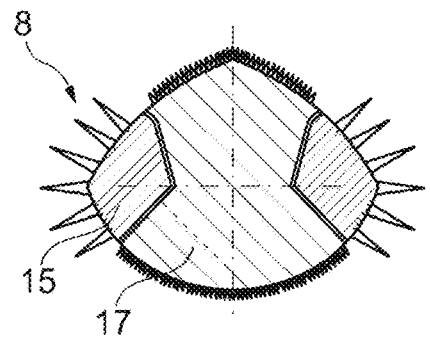
Figure 62:
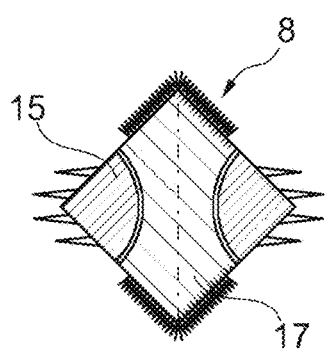
Figure 63:
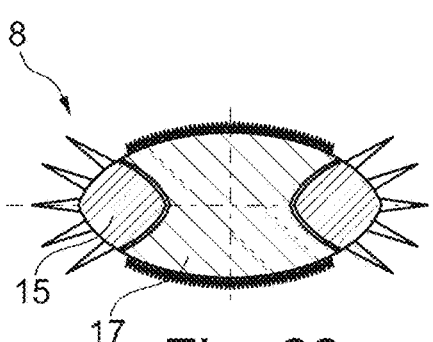
Figure 64:
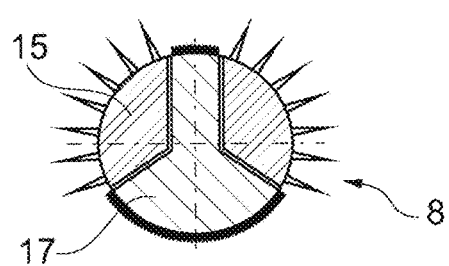
Figure 65:
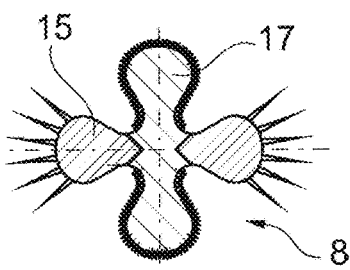
Figure 66:
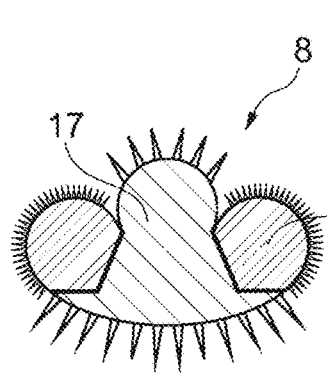
Figure 67:
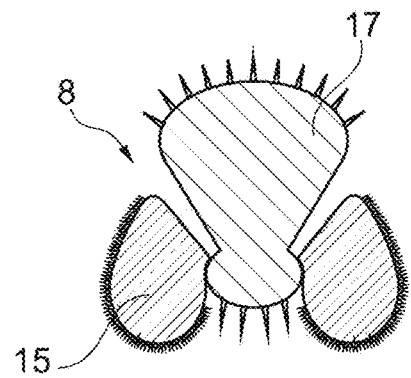

The same goes for the exemplary embodiments in FIGS. 46 and 47. It can be seen in these figures that the flocked coating 218 can cover not only the spikes 217 but also the outer portions of the second part 17, which extend between the spikes or between the latter and the first part 15, as illustrated in FIG. 47 in particular. In the presence of a multilobe second part 17, the spikes 217 are for example oriented substantially radially on each corresponding lobed part. The presence of the grooves formed between one of the lobes of the second part 17 and the two lobes of the first part 15 can allow the product to collect and the autonomy of the applicator to be enhanced.

The examples in FIGS. 48 to 53 differ from those in FIGS. 42 to 47 by the absence of the flocked coating 218 on the second part 17.

The examples in FIGS. 54 to 59 differ from those in FIGS. 36 to 41 by the presence of flocked coatings 215 and 218 on the first 15 and second parts 17.

In the examples illustrated, the flocked coating 218 of the second part 17 does not extend over the surfaces thereof that face the first part 15, in the housing 40. In a variant that is not illustrated, the coating 218 runs onto these surfaces and the assembly of the first and second parts makes it possible to hide the flocked coating that runs onto said surfaces, thereby making it possible to obtain clean contours on each of the faces 18 and 19.

The same may go for the flocked coating 215 which extends over the first part. This coating can run into the housing 40 and be partially hidden by the second part when the latter is in position.

The flocked coatings 215 and 218 of the first 15 and second 17 parts are for example made of flock fibres which differ in terms of their length and/or their diameter, the material used and/or their colour.

Figure 68:
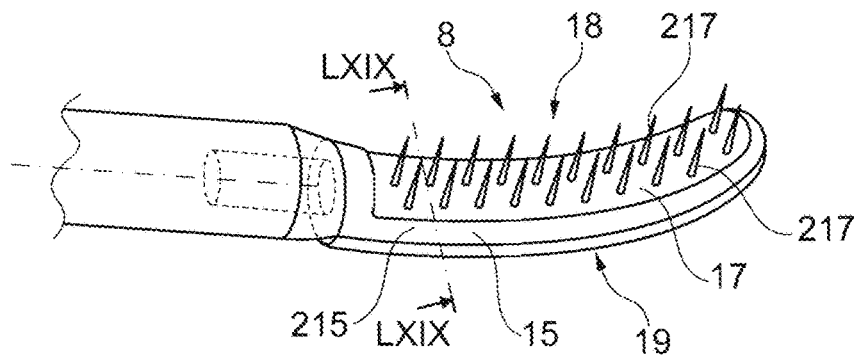
Figure 69:
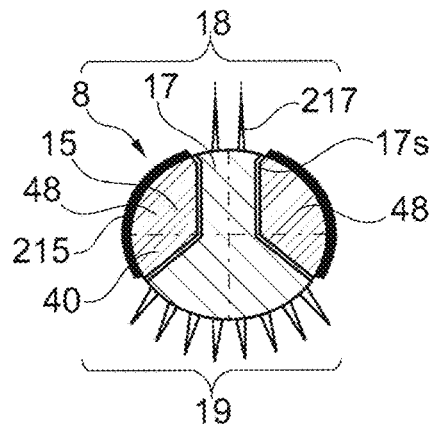
FIG. 69 is a cross section through the applicator from FIG. 68 on LXLX-LXIX.

Another exemplary embodiment of an applicator member is shown in FIGS. 68 and 69. In this example, the first part comprises two arms 48 that define a housing 40 in which the second part 17 is received, the latter bearing spikes 217 on the side of the face 18, while having no spikes on the side of the face 19 which corresponds to the back of the applicator member. The spikes 217 are for example disposed in one or more rows of spikes, for example two or three longitudinally extending rows. The applicator head can have a curved overall shape which is concave on the side of the face 18. The first part 15 can comprise a flocked coating 215 which extends all around the second part 17 on the side of the face 18, as can be seen in particular in FIG. 68. The second part 17 has an upper part 17s which widens, as can be seen in FIG. 69, in order to ensure that the second part 17 is retained in the first 15 by snap-fastening.

Figure 70:
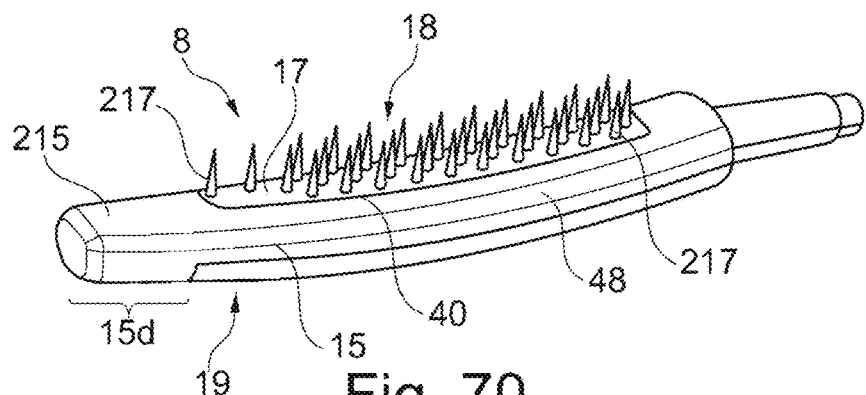
FIG. 70 shows a perspective view of a variant of an applicator member.
Figure 71:
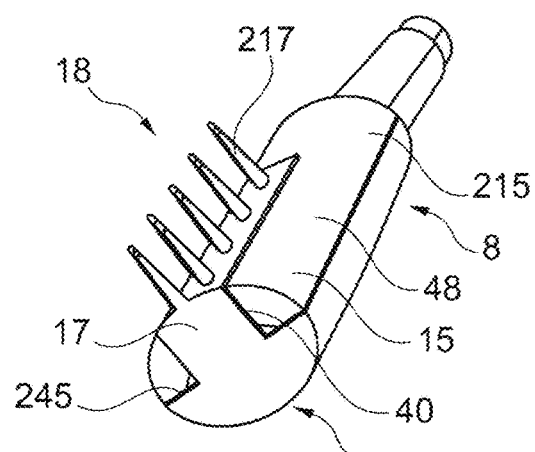
FIG. 71 is a view with a cross section through the applicator from FIG. 70.

The exemplary embodiment in FIGS. 70 and 71 is fairly close to that in FIGS. 68 and 69. However, the face 19 is defined over the major part of the applicator member by the second part 17, the first part 15 only being visible, on the side of the face 19, at the end of the applicator member, over a distal portion 15d in which the second part 17 is absent.

The second part 17 can extend, along the portion of its length in which it is engaged in the first part, along a length that is greater than or equal to that of the first part, as can be seen in FIG. 71.

The second part can have a shoulder 245 which is situated in a plane of greatest width for the applicator member 8.

Figure 72:
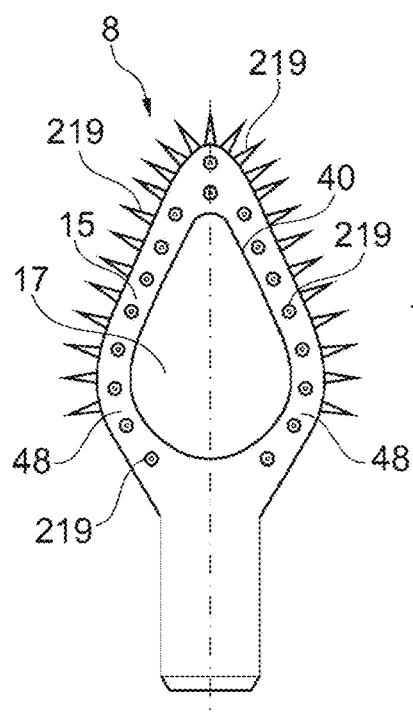
FIG. 72 shows a front view of a variant of an applicator member.
Figure 73:
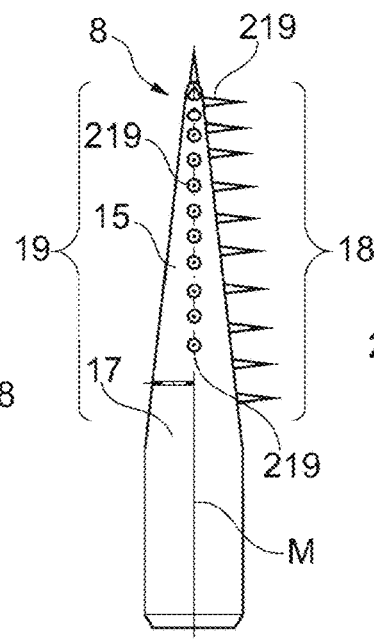
FIG. 73 is a side view of the applicator from FIG. 72

In the example in FIGS. 72 and 73, the first part 15 has spikes 219 on the side of the face 18, these spikes being visible in FIG. 72, and also around the perimeter of the first part 15, the second part 17 not having such spikes. The second part 17 may or may not comprise a flocked coating.

The first part 15 has two arms which converge in the direction of the distal end of the applicator member when the latter is viewed from the front, as in FIG. 72, forming a housing 40 between one another which is in the overall shape of a droplet, for example, as illustrated.

The spikes 219 which extend around the perimeter of the first part 15 can each have their longitudinal axis contained in a median plane M that intersects the applicator member substantially half-way through its thickness. The other spikes 219 can be oriented substantially perpendicularly to this plane M, as illustrated.

Of course, other examples of spike arrangements are possible without departing from the scope of the present invention.

Figure 74:
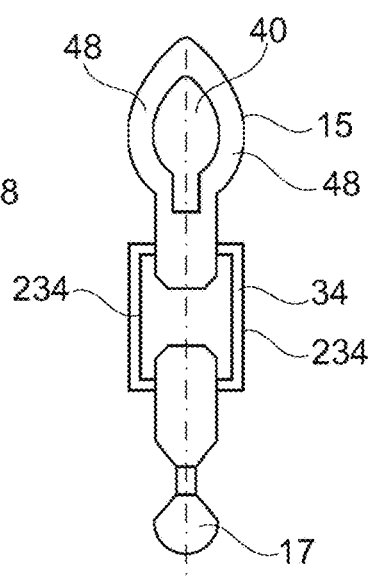
FIG. 74 illustrates a variant embodiment of the hinge, FIG. 75 examples of tested applicators.
Figure 75:
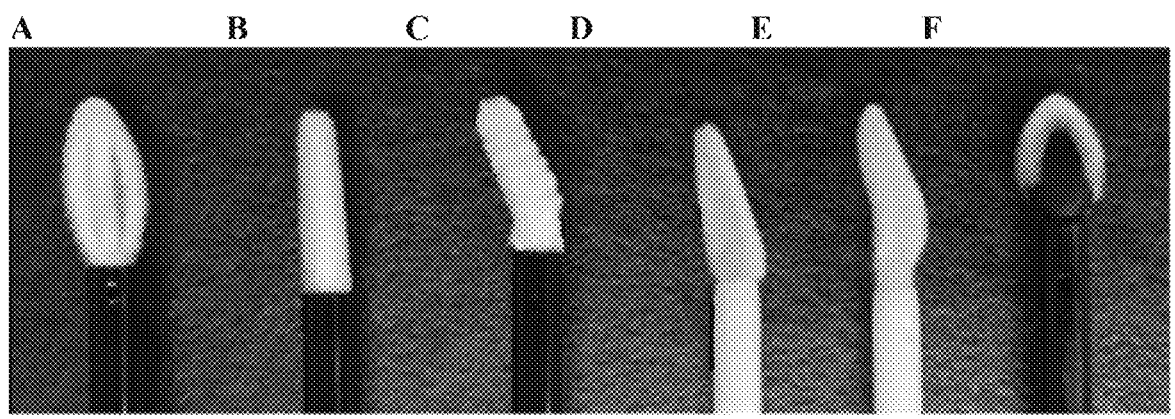

The hinge can be realized as illustrated in FIG. 74, with two flexible strands 234 which are each attached to the parts 15 and 17 at a distance from their proximal end. The strands form a sort of frame in top view, in the moulding configuration.

The invention is not limited to the examples illustrated.

In particular the features of the various examples illustrated can be combined as parts of variants which are not illustrated.

For example, in a general manner, the two parts can be flocked, the flockings being different; one of the parts may comprise a relief of a certain type on one side and a different type of relief on the other side so as to have different effects on one side of the applicator and the other.

Composition

Siloxysilicate Resins

The cosmetic compositions of the present invention comprise at least one silicone resin such as described for example, in U.S. Pat. No. 5,505,937, U.S. Pat, No, 5,911, 974, U.S. Pat. No. 5,965,112, U.S. Pat, No, 5,985,298, U.S. Pat. No. 6,074,654, U.S. Pat. No. 6,780,422, U.S. Pat. No. 6,908,621, the disclosures of which are hereby incorporated by references.

According to this invention, the cosmetic compositions may contain siloxysilicate resins. One non-limiting example of a siloxysilicate in accordance with the present invention is trimethylsiloxysilicate, which may be represented by the following formula:

wherein x and y may, for example, range from 50 to 80. Such siloxysilicates are commercially available from General Electric, Dow Corning, Wacker, Milliken, Siltech, Grant Industries, Momentive and Shin-Etsu Silicones under the tradename Resin MQ®.

According to another embodiment of this invention, the compositions may contain silsesquioxane resins, including comprise at least one polypropyl silsesquioxane film forming resin.

Silsesquioxane resins are a specific form of silicone resin. Silicone resin nomenclature is known in the art as "MDTQ" nomenclature, whereby a silicone resin is described according to the various monomeric siloxane units which make up the polymer. Each letter of "MDTQ" denotes a different type of unit. When the film forming resin is made up predominantly of tri-functional units (or T units), it is generally called a silsesquioxane resin, which is described, for example in US 2006/0292096, herein incorporated by reference.

Examples of silsesquioxane resins that may be used in the present invention are alkyl silsesquioxane resins that are silsesquioxane homopolymers and/or copolymers having an average siloxane unit of the general formula $R_n^1SiO_{(4-n)/2}$, wherein each R1 is a propyl group, wherein more than 80 mole % of R1 represent a C3-C10 alkyl group, n is a value of from 1.0 to 1.4, and more than 60 mole % of the copolymer comprises $R^1SiO_{3/2}$ units. As each R1 is a propyl group these polymers are called polypropylsilsesquioxane resins or "t-propyl" silsesquioxane resins. These resins and methods of making them are described, for example in U.S. Pat. No. 8,586,013, 2012/0301415, 2007/0093619, and 2006/0292096, all of which are herein incorporated by reference.

A non-limiting example of a polypropylsilsesquioxane resin suitable for use in the present invention is commercially available from Dow Corning as Dow Corning 670 Fluid or Dow Corning 680 Fluid. These Dow Corning resins have a general formula of $R_nSiO_{(4-n)/2}$ wherein R is independently chosen from a hydrogen atom and a monovalent hydrocarbon group comprising 3 carbon atoms, wherein more than 80 mole % of R are propyl groups, n is a value from 1.0 to 1.4, more than 60 mole % of the copolymer comprises $RSiO_{3/2}$ units, and having a hydroxyl or alkoxy content from 0.2 to 10% by weight, for example between 1 and 4% by weight, preferably between 5 and 10% by weight, and more preferably between 6 and 8% by weight. Preferably, the polypropylsilsesquioxane resin has a molecular weight from about 5000 to about 30,000 and a Tg from about −5° C. to about 5° C.

Another embodiment of this invention, exemplifies the composition containing at least one siloxysilicate resin, at least one silsesquioxane resin and/or mixture thereof.

The at least one silicone resin is generally present in the cosmetic composition of the present invention in an amount ranging from about 5% to about 30% by weight; such as from about 10% to about 25% by weight; such as from about 15% to about 20% by weight, all weights being based on the weight of the composition as a whole.

Polyorganosiloxane Copolymer

The cosmetic compositions of the present invention also comprise at least one polyorganosiloxane-containing polymer. The polyorganosiloxane-containing polymer useful herein is a polymer (homopolymer or copolymer) having at least one moiety which contains: at least one polyorganosiloxane group consisting of 1 to about 1000 organosiloxane units in the chain of the moiety or in the form of a graft, and at least two groups capable of establishing hydrogen interactions. Non-limiting examples of polyorganosiloxane-containing polymers are disclosed, for example in US. Pat. No. 8,945.525, the disclosure of which is hereby incorporated by reference.

Additional polyorganosiloxane-containing polymers which may be used in the composition of the invention include those described in documents U.S. Pat. No. 5,874,069, U.S. Pat. No. 5,919,441, U.S. Pat. No. 6,051,216, and U.S. Pat. No. 5,981,680, the entire contents of which are hereby incorporated by reference.

A preferred polyorganosiloxane-containing polymer for use in the present invention contain at least one moiety chosen from formula (III):

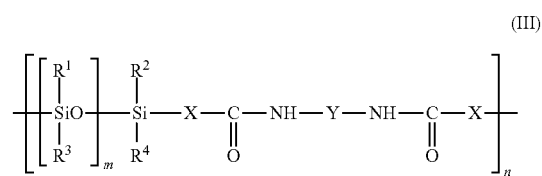

and formula (IV)

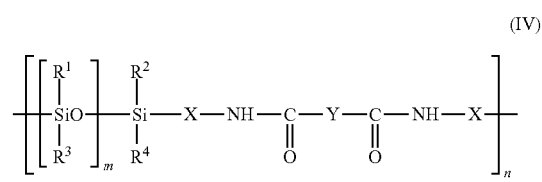

in which:

(a) $R^1$, $R^2$, $R^3$ and $R^4$ are the same or different and may be selected from the group consisting of methyl, ethyl, propyl, isopropyl, a siloxane chain, and phenyl;

(b) X is a linear or branched chain alkylene having 1-30 carbons;

(c) Y is selected from the group consisting of linear or branched chain alkylenes having 1-40 carbons;

(d) m is a number between 1 and 700;

(e) n is a number between 1 and 500.

Particularly preferred polyorganosiloxane-containing polymers useful herein are commercially available from Dow Corning under the tradenames DC 8178® and DC 8179®, which are known under the INCI denomination of Nylon-611/Dimethicone Copolymer.

The at least one polyorganosiloxane-containing polymer is generally present in the cosmetic composition of the present invention in an amount ranging from about 2% to about 35% by weight; such as from about 5% to about 30% by weight; such as from about 7% to about 20% by weight, all weights being based on the weight of the composition as a whole.

Silicone Elastomer (Silicone Crosspolymer)

The composition according to the invention also comprises at least a silicone elastomer.

In a preferred embodiment, the composition comprises a non-emulsifying silicon elastomer.

The non-emulsifying silicon elastomer may be in the form of a gel or a powder.

The "organopolysiloxane elastomer" or "silicon elastomer" or "silicone crosspolymer" thickens the composition, adds the cushiony (spongy) effect and to improves the application of the finished product. Also, it provides a very soft feel and mattifying effect after the application, which is especially advantageous for skin products.

The term "non-emulsifying" defines organopolysiloxane elastomers that do not contain in any hydrophilic chains, and in particular polyoxyalkylene (especially polyoxyethylene or polyoxypropylene) or polyglyceryl units. Thus, according to one particular embodiment of the invention, the composition comprises an organopolysiloxane elastomer that is free of polyoxyalkylene units and polyglyceryl units.

The non-emulsifying elastomers are described in US. Pat. No. 8,637,057, the disclosure of which is hereby incorporated by reference.

The non-emulsifying elastomers particularly useful in this invention include but not limit those sold under the names KSG-6, KSG-15, KSG-16, KSG-18, KSG-41, KSG-42, KSG-43 and KSG-44 by the company Shin-Etsu, DC 9040, DC 9041, DC 9509, DC 9505 and DC 9506, by the company Dow Corning, and SFE 839 by the company General Electric.

In an embodiment, the organopolysiloxane elastomer particles are conveyed in the form of a gel formed from an elastomeric organopolysiloxane included in at least one hydrocarbon-based oil and/or one silicone oil. In these gels, the organopolysiloxane particles are often non-spherical particles.

Not limited examples of silicone elastomers useful in this invention are dimethicone crosspolymer gels (blends of dimethicone crosspolymers in solvents) having viscosity values from about 150 and to about 700 mm$^2$/s, from about 200 to about 650 mm$^2$/s and from about 300 to about 600 mm$^2$/s.

Particularly useful for this invention may be blends of high molecular weight silicone elastomers in volatile solvents, such as silicone oils, hydrocarbon oils and mixtures thereof, as per definition disclosed far along.

The specific but not limiting examples of silicone elastomeric gels applicable in this invention are represented by DC EL-8040 ID (INCI name: Isododecane (and) Dimethicone Crosspolymer) and DC EL-9140 DM (INCI name: Dimethicone (and) Dimethicone Crosspolymer), supplied by Dow Corning.

Non-limiting examples of silicone elastomers and their synthesis are disclosed, for example in U.S. Pat. No. 8,637,057 and US/20150174048, all of which are herein incorporated by reference.

This silicon elastomers present in the inventive compositions are generally in a content ranging from 1 percent to 30 percent by weight of active material (dry matter), more preferably from about 1.5 percent to about 20 percent and most preferably from 2 percent to 10 percent by weight relative to the total weight of said composition.

Volatile Solvent

The compositions of the invention co east one volatile solvent.

The expression "volatile solvent" means any non-aqueous medium capable of evaporating on contact with the skin or the lips in less than one hour at room temperature and atmospheric pressure.

Examples of suitable volatile solvents include volatile hydrocarbon-based oils such as, for example, volatile hydrocarbon oils having from 8 to 16 carbon atoms and their mixtures and in particular branched $C_8$ to $C_{16}$ alkanes such as $C_8$ to $C_{16}$ isoalkanes (also known as isoparaffins), isododecane, isodecane, isohexadecane, and for example, the oils sold under the trade names of Isopar or Permethyl, the $C_8$ to $C_{16}$ branched esters such as isohexyl or isodecyl neopentanoate, alcohols, and their mixtures. Preferably, the volatile hydrocarbon-based oils have a flash point of at least 40° C.

Examples of volatile hydrocarbon-based oils include, but are not limited to those given in Table 1 below.

TABLE 1

| Compound | Flash Point (° C.) |
|---|---|
| Isododecane | 43 |
| Isohexadecane | 102 |
| Isodecyl neopentanoate | 118 |
| Propylene glycol n-butyl ether | 60 |
| Ethyl 3-ethoxypropionate | 58 |
| Propylene glycol methylether acetate | 46 |
| Isopar L (isoparaffin $C_{11}$-$C_{13}$) | 62 |
| Isopar H (isoparaffin $C_{11}$-$C_{12}$) | 56 |

The volatile solvent may also be chosen from volatile silicone oils, which may be linear or cyclic, having a viscosity, at room temperature, of less than or equal to 6 cSt, and having from 2 to 7 silicon atoms, optionally substituted with alkyl or alkoxy groups of 1 to 10 carbon atoms.

Examples of suitable volatile silicone oils include, but are not limited to, those listed in Table 2 below.

TABLE 2

| Compound | Flash Point (° C.) | Viscosity (CSt) |
|---|---|---|
| Octyltrimethicone | 93 | 1.2 |
| Hexyltrimethicone | 79 | 1.2 |
| Decamethylcyclopentasiloxane (cyclopentasiloxane or D5) | 72 | 4.2 |
| Octamethylcyclotetrasiloxane (cyclotetradimethylsiloxane or D4) | 55 | 2.5 |
| Dodecamethylcyclohexasiloxane (D6) | 93 | 7 |
| Decamethyltetrasiloxane (L4) | 63 | 1.7 |
| KF-96 A from Shin Etsu | 94 | 6 |
| PDMS (polydimethylsiloxane) DC 200 (1.5 cSt) from Dow Corning | 56 | 1.5 |
| PDMS DC 200 (2 cSt) from Dow Corning | 87 | 2 |
| PDMS DC 200 (5 cSt) from Dow Corning | 134 | 5 |
| PDMS DC 200 (3 St) from Dow Corning | 102 | 3 |

The at least one volatile solvent is generally present in the cosmetic composition of the present invention in an amount ranging from about 5% to about 50% by weight; such as from about 10% to about 45% by weight; such as from about 15% to about 40% by weight, all weights being based on the weight of the composition as a whole.

Non-Volatile Solvent

The compositions of the present invention also co p se at least one non-volatile solvent (oil).

The volatility of the oils can be determined using the evaporation speed as set forth in U.S. Pat. No. 6,338,839, the content of which is herein incorporated by reference.

Non-volatile oils include low viscosity oils (having a viscosity from about 5 to about 10 centipoise) and high viscosity oils (having a viscosity of from about 100 to about 10,000 centipoise), and mixtures thereof. In contrast to waxes, oils are liquids at room temperature.

According to a particular embodiment of the present invention, the oil is a high viscosity oil which is a silicone oil and/or a hydrocarbon oil. "High viscosity" means an oil having a viscosity greater than 100 cSt, particularly greater than 250 cSt at 25° C. Most particularly, the non-volatile oil is selected from a silicone oil. Such oils are described, for example in US 2011/0293550 and US 2004/0126350, both of which are herein incorporated by reference.

Non-limiting examples of suitable non-volatile silicone oils include polymethylsiloxanes (PDMS) with a linear or cyclic silicone chain, which are liquid or pasty at room temperature, especially cyclopolydimethylsiloxanes (cyclomethicones) such as cyclohexasiloxane; polydimethylsiloxanes (CTFA designation "dimethicones") comprising alkyl or alkoxy groups, which are pendent or at the end of a silicone chain, these groups containing from 2 to 24 carbon atoms; polydiethyl siloxanes; and dimethicone fluids having viscosity from about 300 cPs at 25° C. to about 1500 cPs at 25° C. Particularly useful dimethicone fluids have viscosity from about 350 cPs at 25° C. to about 1000 cPs at 25° C.

Specific examples of suitable for this invention high viscosity silicone oils include, but are not limited to, Xiameter® silicone fluids from Dow Corning.

The at least one non-volatile silicone oil is present in the compositions of the present invention in an amount ranging from about 2% to about 30% by weight, including from about 4% to about 25% by weight, typically about 6% to about 20% by weight, based on the total weight of the composition, including all ranges and subranges within these ranges.

It has been surprisingly discovered that by combining in the inventive composition, at least one silicone elastomer, preferably at least one dimethicone crosspolymer, and at least one non-volatile silicone fluid having a viscosity greater than or equal to 350 cSt at 25° C., in a ratio where the weight of the silicone elastomer to the weight of the non-volatile silicone fluid is higher or equal to from about 1:0.02 and is lower or equals to from about 1:10 by weight (for example, 1:0.02 to 1:10), including all ranges and subranges therebetween such as, for example, from about 1:1 to about 1:6 and from about 1:1 to about 1:5, the weights being relative to the total weight of the composition, yield a cosmetic characterized by long wear, transfer resistance, non-tackiness, limited flaking and great comfort.

According to other embodiments, the present invention refers to methods of improving the tackiness, transfer-resistance and/or long wear properties of a composition, comprising incorporating to the composition, at least one silicone elastomer, preferably at least one dimethicone crosspolymer, and at least one non-volatile silicone fluid having a viscosity greater than or equal to 350 cSt at 25° C., in a ratio where the weight of the silicone elastomer to the weight of the non-volatile silicone fluid is higher or equal to from about 1:0.02 and is lower or equals to from about 1:10 by weight (for example, 1:0.02 to 1:10), including all ranges and subranges therebetween such as, for example, from about 1:1 to about 1:6 and from about 1:1 to about 1:5, yield a cosmetic characterized by long wear, transfer resistance, non-tackiness, limited flaking and great comfort.

The compositions of the present invention are useful as compositions for making up the skin, in particular the lips.

Wax (Optional)

The cosmetic compositions of the present invention optionally may contain at least one wax.

For the purposes of the present invention, a wax is a lipophilic fatty compound that is solid at room temperature (25° C.), has a reversible solid/liquid change of state (that is, the state of the material may change based on temperature), has a melting point greater than 45° C., preferably greater than 55° C., more preferably between about 65° C. to about 120° C., and has anisotropic crystal organization in the solid state. The melting point of the wax may be measured using a differential scanning calorimeter (DSC), for example the calorimeter sold under the name DSC 30 by Mettler. For waxes that are derived from petroleum, such as microcrystalline wax, the melting point may be measured according to the drop ASTM method, D-127.

The waxes are those generally used in cosmetics and dermatology. The waxes may be of natural origin, for instance beeswax, carnauba wax, candelilla wax, ouricoury wax, Japan wax, cork fiber \max or sugar cane wax, paraffin wax, lignite wax, microcrystalline waxes, lanolin wax, montan wax, ozokerites and hydrogenated oils, for instance hydrogenated jojoba oil.

The waxes also may be of synthetic origin, for instance polyethylene waxes derived from the polymerization of ethylene, waxes obtained by Fischer-Tropsch synthesis, esters of fatty acids and of glycerides that are solid at 40° C.

Waxes of synthetic origin are preferable as they are more uniform and provide greater reproducibility than waxes of natural origin. Moreover, the waxes are preferably not silicone waxes.

Particular waxes include polyethylene waxes, for example the product sold under the name Performalene 500-L Polyethylene (New Phase Technology), and polymethylene waxes, for instance the product sold under the name Cirebelle 303 (Sasol).

The cosmetic compositions of the present invention may contain at least one polypropylsilsesquioxane wax substituted with alkyl units having at least 30 carbons.

Polypropylsilsesquioxane waxes, in general, have been disclosed in patent publication WO2005/100444 and U.S. Pat. No. 8,586,013, the entire contents of which are hereby incorporated by reference.

It should be noted, however, that not all polypropylsilsesquioxane waxes yield stable colored cosmetic emulsion products. More particularly, it has been found that only those polypropylsilsesquioxane waxes substituted with alkyl units having at least 30 carbons are stable.

A particularly preferred polypropylsilsesquioxane wax for use in the present invention is a C30-45 ALKYLDIMETHYLSILYL POLYPROPYLSILSESQUIOXANE commercially available from DOW CORNING under the tradename SW-8005 C30 Resin Wax.

When present in the instant compositions, the at least one wax may be present in an amount ranging from about 0.01% to about 30% by weight, from about 0.02% to about 25%, typically from about 0.03% to 15% by weight, preferably from about 0,05% to about 5% by weight, including all ranges and subranges therebetween, all weights based on the weight of the composition as a whole.

Pigments

The cosmetic compositions of the present invention may also contain at least one cosmetically acceptable colorant such as a pigment or dyestuff. Examples of suitable pigments include, but are not limited to, inorganic pigments, organic pigments, lakes, pearlescent pigments, iridescent or optically variable pigments, and mixtures thereof. A pigment should be understood to mean inorganic or organic, white or colored particles. Said pigments may optionally be surface-treated within the scope of the present invention but are not limited to treatments such as silicones, perfluorinated compounds, lecithin, and amino acids.

Representative examples of inorganic pigments useful in the present invention include those selected from the group consisting of rutile or anatase titanium dioxide, coded in the Color Index under the reference CI 77,891; black, yellow, red and brown iron oxides, coded under references CI 77,499, 77, 492 and, 77,491; manganese violet (CI 77,742); ultramarine blue (CI 77,007); chromium oxide (CI 77,288); chromium hydrate (CI 77,289); and ferric blue (CI 77,510) and mixtures thereof.

Representative examples of organic pigments and lakes useful in the present invention include, but are not limited to, D&C Red No. 19 (CI 45,170), D&C Red No. 9 (CI 15,585), D&C Red No. 21 (CI 45,380), D&C Orange No. 4 (CI 15,510), D&C Orange No. 5 (CI 45,370), D&C Red No. 27 (CI 45,410), D&C Red No. 13 (CI 15,630), D&C Red No. 7 (CI 15,850), D&C Red No. 6 (CI 15,850), D&C Yellow No. 5 (CI 19,140), D&C Red No. 36 (CI 12,085), D&C Orange No. 10 (CI 45,425), D&C Yellow No. 6 (CI 15,985), D&C Red No. 30 (CI 73,360), D&C Red No.3 (CI 45,430) and the dye or lakes based on cochineal carmine (CI 75,570) and mixtures thereof.

Representative examples of pearlescent pigments useful in the present invention include those selected from the group consisting of the white pearlescent pigments such as mica coated with titanium oxide, mica coated with titanium dioxide, bismuth oxychloride, titanium oxychloride, colored pearlescent pigments such as titanium mica with iron oxides, titanium mica with ferric blue, chromium oxide and the like, titanium mica with an organic pigment of the above-mentioned type as well as those based on bismuth oxychloride and mixtures thereof.

The precise amount and type of colorant employed in the compositions of the present invention will depend on the color, intensity and use of the cosmetic composition and, as a result, will be determined by those skilled in the art of cosmetic formulation. However, one preferred amount of colorant for use in the present invention is from about 0.5% to about 15%, typically from about 1.5% to about 12%, most typically from about 2% to about 10%, based on the weight of the composition.

Filler

Fillers that may be used in the compositions of the invention include, for example, silica powder; talc; polyamide particles and especially those sold under the name Orgasol by the company Atochem; polyethylene powders; microspheres based on acrylic copolymers, such as those based on ethylene glycol dimethacrylate/lauryl methacrylate copolymer sold by the company Dow Corning under the name Polytrap; expanded powders such as hollow microspheres and especially the microspheres sold under the name Expancel by the company Kemanord Plast or under the name Micropearl F 80 ED by the company Matsumoto; powders of natural organic materials such as crosslinked or noncrosslinked corn starch, wheat starch or rice starch, such as the powders of starch crosslinked with octenyl succinate anhydride, sold under the name Dry-Flo by the company National Starch; silicone resin microbeads such as those sold under the name Tospearl by the company Toshiba Silicone; clays (bentone, laponite, saponite, etc.); and mixtures thereof.

The fillers may be present in the composition of the invention in an amount ranging from about 0.1% to about 50% by weight, such as from 0.5% to about 30% by weight, and such as from about 1% to about 20% by weight, all weights based on the weight of the composition as a whole.

As per this invention hydrophobic silica aerogels are particularly useful.

Silica aerogels are porous materials obtained by replacing (by drying) the liquid component of a silica gel with air. They are generally synthesized via a sol-gel process in liquid medium and then dried, usually by extraction of a supercritical fluid, the one most commonly used being supercritical $CO_2$. This type of drying makes it possible to avoid shrinkage of the pores and of the material. The sol-gel process and the various drying processes are described in detail in Brinker C J., and Scherer G. W., Sol-Gel Science: New York: Academic Press, 1990. Silica aerogels, in general, have been disclosed in U.S. Pat. No. 9,320,689, the entire content of which is hereby incorporated by reference.

As hydrophobic silica aerogels that may be used in the invention, examples that may be mentioned include the aerogel sold under the name VM-2260 (INCI name: Silica silylate), by the company Dow Corning, the particles of which have a mean size of about 1000 microns and a specific surface area per unit of mass ranging from 600 to 800 $m^2/g$.

Mention may also be made of the aerogels sold by the company Cabot under the references AEROGEL TLD 201, AEROGEL OGD 201, AEROGEL TLD 203, ENOVA® AEROGEL MT 1100, ENOVA AEROGEL MT 1200.

Use will be made more particularly of the aerogel sold under the name VM-2270 (INCI name: Silica silylate), by the company Dow Corning, the particles of which have a mean size ranging from 5-15 microns and a specific surface area per unit of mass ranging from 600 to 800 $m^2/g$.

The silica aerogel particles can be used in the inventive compositions from 0.1% to about 8% by weight, preferably from 0.25% to 6% by weight, better still from 0.5% to 4% by weight, including all ranges and subranges therebetween, all weights based on the weight of the composition as a whole.

Additives

The compositions of the present invention may further comprise at least one cosmetically or dermatologically acceptable additive such as aa additional thickener, an additional film former, a plasticizer, an antioxidant, an essential oil, a botanical extract, a fragrance, a preserving agent, a fragrance, a pasty fatty substance, a neutralizing agent, and a polymer, and cosmetically active agents and/or dermatological active agents such as, for example, emollients, moisturizers, vitamins, essential fatty acids and medicaments.

As per this invention, the additives are incorporated from about 0.02% to about 2%, preferably from about 0.1% to about 1.5%, better still from about 0.3% to about 1%.

EXAMPLES

The present invention will be better understood from the examples which follow. The examples are intended to be nonrestrictive and explanatory only, with the scope of the invention defined by the claims.

Method of Preparation of Inventive Composition(s)

The mixture of pigment, isododecane and MQ resin was grinded to create a pigment paste. The blend was processed using Disconti Mill until the paste passed the Hegman Gauge test (ASTM D1210-05). Then, the paste grind was added to the remaining ingredients. The mixture was heated to 80° C. and stirred, until a homogeneous liquid composition was obtained. After that, the inventive composition was cooled down to the room temperature and transferred to desired containers and/or applicators.

Evaluation of inventive compositions: Methods and Test Results

The inventive compositions were tested for tackiness and flaking versus control and comparative compositions. Each of the tested products was tested five (5) times. Testing methods are described below.

Tack Testing

The films of each formula were deposited onto contrast cards using a 3 MIL drawdown bar and an Automatic Drawdown Machine. The films were dried at room temperature (25° C.) overnight and analyzed using a Texture Analyzer equipped with a ball probe. Tack force was measured after applying 350 g-force for 10 seconds. Then, the values of the tackiness were correlated to the comfort of wear of the tested products. The samples having the tackiness having values higher than 100 gr/force, were considered to be very uncomfortable to wear. The tack values between 50-100 gr/force, indicated medium comfort, and those with values of less than 50 gr/force were considered to be comfortable.

Flake Testing

Additionally, the samples were tested for flake resistant properties. The samples of all tested compositions were deposited onto the surface of Thera-Band® intermediate resistance exercise band (7×5 cm), using a 3 MIL drawdown bar. The samples were allowed to dry for 4 hours at room temperature (25° C.) and then they were stretched to the length of 30 cm. The stretching was repeated ten (10) times for each of the samples. During the stretching process, flacking of the dry samples was observed and correlated with durability of wear of the tested products. To define the degree of samples' flacking, the following four (4) point grading scale was used: 0—no flaking (very good wear), 1—low flaking (good wear), 2—medium flaking (medium/acceptable wear) and 3—high flaking (no wear).

Inventive compositions of the liquid lip products containing DC 8040 Silicone elastomer and 1000 cSt Dimethicone are represented but not limited by examples in Table 1, as shown below.

It was observed that the inventive compositions having the highest ratio of the silicone elastomer containing 18% of actives to the dimethicone oil was the least tacky indicating a very good comfort and had medium flaking, meaning that that the wear was considered to be good. The inventive formulations having lower ratios of the same silicone elastomer to the dimethicone fluid, were characterized by increased tackiness (decreased comfort) and improved flaking (better wear). The tackiness for the control samples without dimethicone oil, was very high meaning that the comfort of wear was very low, and shown no flakiness.

TABLE 1

Lip Compositions containing DC 8040 silicone elastomer (18% active)

| | Test results | | | | | | | | |
|---|---|---|---|---|---|---|---|---|---|
| | Inventive Compositions (% weight) | | | | | | | Control Compositions (% weight) | |
| Ingredients | 1 | 2 | 3 | 4 | 5 | 6 | 7 | 1 | 2 |
| MQ | 17.55 | 17.55 | 17.55 | 17.55 | 17.55 | 17.55 | 17.55 | 17.55 | 17.55 |
| PSPA | 9.78 | 9.78 | 9.78 | 9.78 | 9.78 | 9.78 | 9.78 | 9.78 | 9.78 |
| 1000 cst Dimethicone fluid | 12.21 | 12.21 | 12.21 | 6.65 | 6.65 | 9.98 | 9.98 | 0 | 0 |
| Pigment blend | 6.41 | 6.41 | 6.41 | 6.41 | 6.41 | 6.41 | 6.41 | 6.41 | 6.41 |
| Silicone resin wax | 0.5 | 0.5 | 0.5 | 0.5 | 0.5 | 0.5 | 0.5 | 0.5 | 0.5 |
| 8040 Silicone elastomer *(18% active) | 25 (4.5%) | 13.89 (2.5%) | 36.11 (6.5%) | 25 (4.5%) | 13.89 (6.5%) | 25 (4.5%) | 36.11 (6.5%) | 25 (4.5%) | 13.89 (6.5%) |
| Fillers and Lauryl lysine | 4.83 | 4.83 | 4.83 | 4.83 | 4.83 | 4.83 | 4.83 | 4.83 | 4.83 |
| Fragrance | 0.1 | 0.1 | 0.1 | 0.1 | 0.1 | 0.1 | 0.1 | 0.1 | 0.1 |
| Isododecane | QS | QS | QS | QS | QS | QS | QS | QS | QS |
| Ratio of silicone elastomer (% active):dimethicone | 1:2.7 | 1:4.9 | 1:1.9 | 1:1.5 | 1:1.02 | 1:2.2 | 1:1.5 | — | — |
| Tack 1 | 8.5 | 5.3 | 9.8 | 14 | 12.1 | 7.5 | 34.8 | 77.7 | 81.3 |
| Tack 2 | 6.1 | 6.4 | 10.1 | 18.1 | 13.2 | 6.7 | 7.1 | 76 | 69.4 |
| Tack 3 | 7 | 5.5 | 7.4 | 15.9 | 13.3 | 8.6 | 29.5 | 63.7 | 82.9 |
| Tack 4 | 7 | 5.5 | 7.1 | 18 | 11.1 | 7 | 11.5 | 59.4 | 75 |
| Tack 5 | 5.8 | 7 | 8.6 | 19.7 | 16.7 | 9.5 | 37 | 58.8 | 88 |
| Average Tack | 6.9 | 5.9 | 8.6 | 17.1 | 13.3 | 7.9 | 24 | 67.1 | 79.3 |
| Stdev | 1.1 | 0.7 | 1.4 | 2.2 | 2.3 | 1.2 | 13.8 | 9.1 | 7.2 |
| Flaking | 1 | 2 | 1 | 0 | 0 | 0 | 0 | 0 | 0 |

All numerical values in the above table are weight percent active.

*Dow Corning® EL-8040 ID; INCI Name: Isododecane (and) Dimethicone

TABLE 2

Lip Compositions containing DC 9140 DM silicone elastomer (14% active)

| | Test Results | | | | | | |
|---|---|---|---|---|---|---|---|
| | Inventive Compositions (% weight) | | | | | | Control Composition (% weight) |
| Ingredients | 8 | 9 | 10 | 11 | 12 | 13 | 3 |
| MQ | 17.55 | 17.55 | 17.55 | 17.55 | 17.55 | 17.55 | 17.55 |
| PSPA | 9.78 | 9.78 | 9.78 | 9.78 | 9.78 | 9.78 | 9.78 |
| 1000 cst Dimethicone fluid | 12.21 | 12.21 | 11 | 10 | 9 | 10 | 0 |
| Lauryl lysine | 1.5 | 1.5 | 1.5 | 1.5 | 1.5 | 1.5 | 1.5 |
| Pigment blend | 6.41 | 6.41 | 6.41 | 6.41 | 6.41 | 6.41 | 6.41 |
| Silicone resin wax | 0.5 | 0.5 | 0.5 | 0.5 | 0.5 | 0.5 | 0.5 |
| 9140 DM Silicone elastomer *(14% active) | 32.14 (4.5%) | 17.86 (2.5%) | 35.71 (5%) | 35.71 (5%) | 35.71 (5%) | 32.14 (4.5%) | 17.86 (2.5%) |
| Fillers | 3.33 | 3.33 | 3.33 | 3.33 | 3.33 | 3.33 | 3.33 |
| Fragrance | 0.1 | 0.1 | 0.1 | 0.1 | 0.1 | 0.1 | 0.1 |
| Isododecane | QS | QS | QS | QS | QS | QS | QS |
| Ratio of silicone elastomer (% active):dimethicone | 1:2.7 | 1:4.9 | 1:2.2 | 1:2 | 1:1.8 | 1:2.2 | — |
| Tack 1 | 6.3 | 6 | 8.9 | 6.3 | 14.7 | 5.6 | 103.6 |
| Tack 2 | 6.8 | 5.5 | 6.8 | 7.4 | 8 | 9.1 | 108.2 |
| Tack 3 | 5.7 | 5.6 | 7.2 | 7 | 10 | 6.9 | 104 |
| Tack 4 | 6 | 6.1 | 7.9 | 7.8 | 11.7 | 7.2 | 89.1 |
| Tack 5 | 8.8 | 5.8 | 8.2 | 8.7 | 9.4 | 10.2 | 74.2 |
| Ave Tack | 6.7 | 5.8 | 7.8 | 7.4 | 10.8 | 7.8 | 95.8 |
| Stdev | 1.2 | 0.3 | 0.8 | 0.9 | 2.6 | 1.8 | 14.1 |
| Flaking | 1 | 0 | 2 | 2 | 2 | 1 | 0 |

All numerical values in the above table are weight percent active.
*Dow Corning ® EL-9140 DM; INCI Name: Dimethicone (and) Dimethicone Crosspolymer Inventive compositions of the liquid lip compositions containing DC 9140 DM Silicone elastomer and 1000 cSt Dimethicone are represented but not limited by examples in Table 2, as shown below.

As per results presented in Table 2, the inventive samples having the highest ratio of the silicone elastomer (containing 14% of actives) to the dimethicone oil was characterized by the lowest tackiness and providing a very good comfort. The samples did not flake, meaning that they demonstrate a very good wear. The inventive formulations having lower ratios of the same silicone elastomer to dimethicone, had increased both, tackiness and flaking. The tackiness for the control sample was very high and had no flaking. That indicates that the absence of dimethicone significantly increased discomfort of wear, although the wear appeared to be improved.

Based on the result presented in the tables above, the absence of dimethicone oil significantly increased the tack. In addition, the decrease of the concentration of actives in silicone elastomer blends and the increase of dimethicone oil having high viscosity, caused the reduction of tackiness. As per the provided examples, the inventive lip liquid compositions having ratios of the silicone elastomer actives to dimethicone oil from about 1:0.05 to about 1:5 were considered to be very comfortable to wear with minimal or no flacking (good wear).

In order to determine the unique effectiveness of the inventive composition in combination with the inventive applicator, the inventive system was tested versus systems of control applicators and the inventive compositions. The thickness and uniformness of the deposit of the inventive composition delivered by the use of the inventive applicator was compared against product distribution of the inventive compositions provided by the control applicators A, B, C, D and E (as described above).

The tests were conducted via in vitro and in vivo methods, as described below.

In vitro evaluation was conducted as per description below:

1. A polyurethane substrate (White Bioskin Plate Regular; size 3 cm×6 cm) was weighed using an analytical balance.
2. An inventive liquid lip composition was applied onto the Bioskin substrate using each of the tested applicators until the white surface of Bioskin was uniformly covered. For each tested combination of the applicators and the inventive composition prepared two (2) samples.
3. In order to define the amount of the applied lip composition on each of the Bioskin samples, the weight of the treated Bioskin was taken and the amount of applied lip product was calculated by subtracting the weight of Bioskin treated with lipstick minus the weight of the untreated Bioskin substrate.
4. Then the samples were allowed to dry for 5 hours at ambient conditions (25° C., 35% RH) and the amount of the remaining product was calculated according to the procedure described above.

TABLE 3

In vitro evaluation of the systems of lip applicators and inventive composition immediately after product application

| Applicator | Amount of applied product (mg) - Sample 1 | Amount of applied product (mg) - Sample 2 | Average amount of applied product (mg) | Stdev |
|---|---|---|---|---|
| A | 80.50 | 79.70 | 80.10 | 0.2828 |
| B | 76.00 | 77.90 | 76.90 | 0.6718 |
| C | 97.60 | 80.00 | 88.80 | 6.2225 |
| D | 71.90 | 110.40 | 91.20 | 13.6118 |
| E | 95.50 | 98.20 | 96.90 | 0.9546 |
| F (inventive) | 62.80 | 50.40 | 56.60 | 4.3841 |

TABLE 4

In vitro evaluation of lip product applicators five (5) hours after product application

| Applicator | Amount of applied product (mg) - Sample 1 | Amount of applied product (mg) - Sample 2 | Average (mg) | Stdev |
|---|---|---|---|---|
| A | 30.20 | 31.20 | 30.70 | 0.7071 |
| B | 28.60 | 30.60 | 29.60 | 1.4142 |
| C | 43.70 | 32.80 | 38.25 | 7.7075 |
| D | 30.70 | 51.40 | 41.05 | 14.6371 |
| E | 41.40 | 44.80 | 43.10 | 2.4042 |
| F (inventive) | 20.80 | 17.40 | 19.10 | 2.4042 |

As per results above, the inventive applicator (F) delivered the least amount of the inventive product in comparison to the controls. This was observed immediately after the product's application, as well as after five (5) hours of drying at the ambient condition. As previously discussed, the smaller amount of the product provides a thinner film on the surface of the treated substrate. That is associated with less tackiness and flaking over time of the product's wear.

In vivo evaluation was conducted as per description below:
1. Four (4) panelists with medium size lips participated in the test. Each of them tested two (2) times the evaluated samples. Panelists were instructed to apply the lipsticks on their lips following own techniques of the lip product application. Test was performed during the course of 3 days; samples were randomized between the participants.
2. In order to define the amount of the applied product, containers with tested applicators and the inventive compositions were weighted before and after the products' application. The amount of the applied product was determined by calculating differences between the initial weights of the containers and after the application.

TABLE 5

In vivo evaluation of lip product applicators

Amount of applied lipstick (mg)

| Applicator | Panelist #1 | Panelist #2 | Panelist #3 | Panelist #4 | Average (mg) | Stdev |
|---|---|---|---|---|---|---|
| A | 32.95 | 23.65 | 14.30 | 34.45 | 26.34 | 9.339 |
| B | 27.65 | 16.75 | 18.55 | 30.60 | 23.39 | 6.774 |
| C | 24.85 | 15.10 | 35.25 | 29.50 | 21.18 | 7.184 |
| D | 26.20 | 14.65 | 16.35 | 34.70 | 22.97 | 9.329 |
| E | 24.15 | 14.80 | 13.80 | 30.15 | 20.73 | 7.824 |
| F (inventive) | 29.80 | 12.15 | 11.45 | 27.55 | 20.24 | 9.790 |

The results presented in Table 5 show that using the inventive applicators allowed for applying the least amount of the inventive composition. These results correlate to the in vitro study. As per consumers' feedback, the lips treated with the system of the inventive composition and the inventive applicator felt very comfortable and non-tacky. Also, the application was very uniform and aesthetic.

What is claimed is:
1. A cosmetic care system comprising:
    (1) at least one liquid composition comprising:
        (a) from about 2% to about 10% by weight of at least one silicone elastomer relative to a total weight of the composition;
        (b) from about 6% to about 20% by weight of non-volatile silicone oil having a viscosity greater than 300 cSt and lower than 1200 cSt at 25° C.;
        (c) from about 2% to about 35% by weight of at least one Nylon-611/Dimethicone copolymer relative to the total weight of the composition;
        (d) from about 0.1% to about 30% by weight of at least one silicone resin relative to the total weight of the composition, wherein the at least one silicone resin is selected from the group consisting of siloxysilicate resins, silsesquioxane resins, and mixture thereof;
        (e) from about 5% or about 50% by weight of at least one volatile solvent relative to the total weight of the composition; and
        (f) from 0% to about 5% by weight of wax relative to the total weight of the composition;
        wherein the weight ratio of the silicone elastomer (a) to the at least one non-volatile silicone oil (b) is from 1:1 to 1:5;
        the weights being relative to the total weight of the composition,
        the composition provides a matte appearance to lips after application, and
        the composition is substantially free of non-volatile phenylated solvent, and
    (2) an applicator.
2. The cosmetic care system of claim 1 wherein the at least one silicone elastomer is at least one non-emulsifying silicone elastomer.
3. The cosmetic care system of claim 1 wherein the at least one silicone elastomer is at least one dimethicone crosspolymer.
4. The cosmetic care system of claim 1 wherein the at least one dimethicone fluid is present in an amount from about 6% to about 15% by weight relative to the total weight of the composition.
5. The cosmetic care system of claim 1, wherein the at least one Nylon-611/ Dimethicone copolymer is present in an amount from about 8% to about 11% by weight relative to the total weight of the composition.

6. The cosmetic care system of claim 1 wherein the at least one silicone resin is present from about 10% to about 25% by weight, relative to the total weight of the composition.

7. The cosmetic care system of claim 1 wherein the at least one volatile solvent is present from about 10% to about 35% by weight, relative to the total weight of the composition.

8. The cosmetic care system of claim 7 wherein the at least one volatile solvent is selected from hydrocarbon oils, silicone oils and mixtures thereof.

9. The cosmetic care system of claim 1, wherein the composition further contains at least one colorant in amount from about 0.5% to about 7.5% by weight, relative to the total weight of the composition.

10. The cosmetic care system of claim 1, wherein the composition further contains at least one wax in amount from about 0.01% to about 5% by weight, relative to the total weight of the composition.

11. The cosmetic care system of claim 1, wherein the composition further contains at least one filler in amount from about 0.05% to about 30% by weight, relative to the total weight of the composition.

12. A cosmetic care kit comprising:
   (1) at least one liquid composition comprising:
      (a) from about 2% to about 10% by weight of at least one dimethicone crosspolymer relative to a total weight of the composition;
      (b) from about 6% to about 20% by weight of non-volatile dimethicone fluid having a viscosity greater than 300 cSt and lower than 1200 cSt at 25° C.;
      (c) from about 2% to about 35% by weight of at least Nylon-611/ Dimethicone copolymer relative to the total weight of the composition;
      (d) from about 0.1% to about 30% by weight of at least one silicone resin relative to the total weight of the composition, wherein the at least one silicone resin is selected from the group consisting of siloxysilicate resins, silsesquioxane resins, and mixture thereof;
      (e) from about 5% or about 50% by weight of at least one volatile solvent relative to the total weight of the composition; and
      (f) from 0% to about 5% by weight of wax relative to the total weight of the composition;
         wherein the weight ratio of the silicone elastomer (a) to the at least one dimethicone fluid (b) is from 1:1 to 1:5;
         the weights being relative to the total weight of the composition,
         the composition provides a matte appearance to lips after application, and
         the composition is substantially free of non-volatile phenylated solvent; and
   (2) an applicator.

13. The cosmetic care system of claim 1, wherein the composition comprises a solvent component which consists essentially of the at least one volatile solvent and the at least one non-volatile oil.

14. The cosmetic care system of claim 12, wherein the composition comprises a solvent component which consists essentially of the at least one volatile solvent and the at least one non-volatile oil.

* * * * *